(12) United States Patent
Sakurada

(10) Patent No.: US 7,407,289 B2
(45) Date of Patent: Aug. 5, 2008

(54) OPTOMETRY APPARATUS

(75) Inventor: Tomohiro Sakurada, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 230 days.

(21) Appl. No.: 11/300,492

(22) Filed: Dec. 15, 2005

(65) Prior Publication Data

US 2006/0139573 A1    Jun. 29, 2006

(30) Foreign Application Priority Data

Dec. 28, 2004 (JP) ............................. 2004-380876

(51) Int. Cl.
*A61B 3/10* (2006.01)
(52) U.S. Cl. ................... 351/211; 351/222; 351/243
(58) Field of Classification Search ............... 359/624, 359/710; 351/211, 222, 241, 246, 243
See application file for complete search history.

(56) References Cited

U.S. PATENT DOCUMENTS

| | | | | |
|---|---|---|---|---|
| 4,105,302 A * | 8/1978 | Tate, Jr. | ...................... | 351/210 |
| 4,523,822 A | 6/1985 | Thurston | ..................... | 351/234 |
| 5,420,651 A | 5/1995 | Kamppeter | ................. | 351/222 |
| 6,309,068 B1 | 10/2001 | Kohayakawa | ............... | 351/221 |
| 2003/0081174 A1 | 5/2003 | Ross et al. | .................. | 351/212 |

FOREIGN PATENT DOCUMENTS

| | | |
|---|---|---|
| EP | 1 444 946 A1 | 8/2004 |
| EP | 1444945 A1 * | 8/2004 |
| EP | 1444946 A1 * | 8/2004 |
| JP | 2004-180955 | 7/2004 |

* cited by examiner

*Primary Examiner*—Ricky L Mack
*Assistant Examiner*—James R Greece
(74) *Attorney, Agent, or Firm*—Edwards Angell Palmer & Dodge LLP

(57) ABSTRACT

The optometry apparatus includes an index projecting optical system for projecting an index for cross cylinder test to an eye for shortening examination time, a variable cross cylinder lens disposed on an optical axis of the index projecting optical system, for forming one pair of projection images of the index by switching of an astigmatic axial angle while predetermined astigmatic power is set, a joystick lever and a button used to input a result of comparison between appearance states of the pair of projection images of the index, and an initial value setting unit for determining an astigmatic axial angle of the variable cross cylinder lens to cause one of the pair of projection images of the index visually recognized and to cause the other thereof in a blurred state based on objective values of astigmatic power and an astigmatic axial angle of the eye, measured in advance, and for setting the determined astigmatic axial angle as an initial value for astigmatic axial angle measurement.

23 Claims, 17 Drawing Sheets

FIG. 11

⟨INITIAL VALUE SETTING DATA⟩

| ASTIGMATIC POWER (OBJECTIVE VALUE) | ANGLE SHIFT AMOUNT |
|---|---|
| −0.25 | 40° |
| −0.50 | 30° |
| −0.75 ~ −1.00 | 25° |
| −1.25 | 20° |
| −1.50 ~ −2.00 | 15° |
| −2.25 ~ −3.75 | 10° |
| −4.00 ~ −7.00 | 5° |
| −7.25 ~ −8.00 | 3° |

FIG. 12

⟨PERMISSIBLE ERROR SETTING DATA⟩

| ASTIGMATIC POWER (OBJECTIVE VALUE) | PERMISSIBLE ERROR |
|---|---|
| −0.25 | 15° |
| −0.50 | 10° |
| −0.75 ~ −1.25 | 5° |
| −1.50 ~ −2.25 | 3° |
| −2.50 ~ −8.00 | 1° |

OPTOMETRY APPARATUS

BACKGROUND OF THE INVENTION

1. Field of the Invention

The present invention relates to an optometry apparatus capable of performing a cross cylinder test for examining an astigmatic state of an eye to be examined.

2. Description of the Related Art

An optometry apparatus capable of performing a cross cylinder test has been known as an optometry apparatus for optometry measurement. For example, an optometry apparatus described in JP 2004-180955 A (claims and paragraphs [0030] and [0039] to [0047] of the specification) includes an operating means such as a joystick lever and a computer having a computer program for automatically performing an eye examination. An objective eye examination can be simultaneously performed for both eyes. In addition, a subjective eye examination can be performed by a person to be examined alone using a screen navigation system or a voice navigation system. The cross cylinder test is performed during the flow of those examinations.

The optometry apparatus described in JP 2004-180955 A is constructed so as to provide training screens for training an operating method for examination before an actual examination is performed. Training of the cross cylinder test is also performed using the training screens. In the cross cylinder test, an index S shown in FIG. 16 (which is called a cross cylinder test chart or the like) is indicated to an eye to be examined. Astigmatic power or an astigmatic axial angle is switched from one to another, and the person to be examined makes a comparative determination of appearance states of the index S, thereby examining an astigmatic state of the eye to be examined. However, a difference between the appearance states to be compared is not very clear. Therefore, on a training screen, a typical difference between appearance states caused when the astigmatic axial angle is changed is presented in an exaggerated manner. One projection image is clearly displayed on the training screen and the other projection image is displayed thereon with a blurred state, thereby promoting understanding of the contents of the cross cylinder test and understanding of the operating method.

However, when the training is performed before the examination, it is likely that the person to be examined will forget the examination contents and the operating method because some time is elapsed before the actual cross cylinder test starts. The training requires time, so there is a problem in that an examination time per a person to be examined becomes longer.

In the cross cylinder test, a difference between appearance states of the index to be compared is not clear and thus it is difficult for the person to be examined to make rapid determination, so that a time for the cross cylinder test lengthens in some cases. In particular, there are cases where the astigmatic axial angle is measured with excessive measurement precision, which hinders the smooth progress of the cross cylinder test. The astigmatic axial angle measurement performed through the cross cylinder test is to compare appearance states of a pair of projection images of the cross cylinder test chart S with each other, so the measurement is in some cases completed with a state in which the projection image are not clearly visually recognized. Therefore, the response given by the person to be examined at the last stage of the test often becomes vague, leading to an increase in examination time.

SUMMARY OF THE INVENTION

The present invention has been made in view of the above-mentioned circumstances. An object of the present invention is to provide an optometry apparatus capable of realizing a smooth progress of a cross cylinder test to shorten an examination time.

To attain the above object, according to a first aspect of the present invention, there is provided an optometry apparatus, including: an optical system for projecting an index for cross cylinder test to an eye to be examined; a cross cylinder lens for forming a pair of projection images of the index by a change in astigmatic axial angle while predetermined astigmatic power is set, the cross cylinder lens being disposed on an optical axis of the optical system; operating means for inputting a result of comparison between appearance states of the pair of projection images of the index, the optometry apparatus measuring an astigmatic axial angle of the eye to be examined based on an input content from the operating means; and initial value setting means for determining an astigmatic axial angle of the cross cylinder lens which causes one of the pair of projection images of the index to be clearly visually recognized and causes the other of the pair of projection images of the index to be visually recognized in a blurred state based on an objective value of astigmatic power of the eye to be examined and an objective value of the astigmatic axial angle of the eye to be examined, which are measured in advance, and for setting the determined astigmatic axial angle as an initial value for astigmatic axial angle measurement.

According to a second aspect of the present invention, in the optometry apparatus according to the first aspect, the optometry apparatus further includes storing means for storing an amount of shift from the objective value of the astigmatic axial angle, which is necessary to cause the one of the pair of projection images to be clearly visually recognized and cause the other of the pair of projection images to be visually recognized in the blurred state, in association with the objective value of the astigmatic power in advance, and the initial value setting means determines the amount of shift associated with the objective value of the astigmatic power from the storing means and shifts the objective value of the astigmatic axial angle by the determined amount of shift to determine the initial value.

According to a third aspect of the present invention, in the optometry apparatus according to the first or second aspect, the optometry apparatus further includes determination means for making error determination when the input content from the operating means is different from a preset input content from comparison between appearance states of the pair of projection images while the initial value is set.

According to a fourth aspect of the present invention, in the optometry apparatus according to any one of the first to third aspects, the optometry apparatus further includes control means for controlling the cross cylinder lens to shift the astigmatic axial angle measurement to a next stage when the input content is identical with the preset input content from comparison between appearance states of the pair of projection images while the initial value is set.

According to a fifth aspect of the present invention, in the optometry apparatus according to the fourth aspect, the optometry apparatus further includes error setting means for setting a permissible error for the astigmatic axial angle measurement of the eye to be examined based on the objective value of the astigmatic power, and the control means controls the cross cylinder lens to successively shift stages of the astigmatic axial angle measurement so that a measurement error of the astigmatic axial angle of the eye to be examined is kept within the permissible error.

According to a sixth aspect of the present invention, in the optometry apparatus according to the fifth aspect, the permissible error is set so that residual astigmatism, which is caused when the objective value of the astigmatic power and the objective value of the astigmatic axial angle are corrected by a corrective lens and an astigmatic axial angle of the corrective lens is shifted, is within a first predetermined range, and that the amount of change in spherical power caused when the objective value of the astigmatic power and the objective value of the astigmatic axial angle are combined with astigmatic power of the corrective lens and an astigmatic axial angle of the corrective lens is within a second predetermined range.

According to a seventh aspect of the present invention, in the optometry apparatus according to the sixth aspect, the first predetermined range for the residual astigmatism is within −0.25 diopters and the second predetermined range for the amount of change in spherical power is smaller than ±0.25 diopters.

According to an eighth aspect of the present invention, in the optometry apparatus according to any one of the fourth to seventh aspects, the control means changes the astigmatic power of the cross cylinder lens in a stage after a predetermined stage of the astigmatic axial angle measurement to a value smaller than the astigmatic power in a stage before the predetermined stage.

According to the present invention, the optometry apparatus includes the initial value setting means for determining the astigmatic axial angle of the cross cylinder lens which causes the one of the pair of projection images of the index for cross cylinder test to be clearly visually recognized and causes the other thereof to be visually recognized in the blurred state based on the objective value of astigmatic power of the eye to be examined and the objective value of the astigmatic axial angle thereof, which are measured in advance, and for setting the determined astigmatic axial angle as the initial value for astigmatic axial angle measurement. The person to be examined compares the clear projection image and the blurred projection image with each other for determination in the first stage of the actual cross cylinder test, so he or she can understand the content of the test and train the operating method of the operating means. Therefore, the understanding of the cross cylinder test and the training of the operating method can be made with the actual examination in an integrated manner, so the person to be examined does not forget the examination content and the operating method once understood with a lapse of time. Thus, the cross cylinder test can be smoothly performed, with the result that the examination time can be shortened. It is unnecessary to perform the training of the cross cylinder test for a long time before the examination unlike in the prior art, so the entire examination time including a training time can be shortened.

According to the fifth aspect of the present invention, the optometry apparatus can perform the astigmatic axial angle measurement within the permissible error associated with the objective value of the astigmatic power of the eye to be examined. Therefore, there is no case where the astigmatic axial angle is measured with excessive measurement precision. Thus, the examination can be smoothly performed as compared with the prior art, so that the examination time can be shortened.

BRIEF DESCRIPTION OF THE DRAWINGS

In the accompanying drawings:

FIG. 11 is a table showing an example of initial value setting data stored in the optometry apparatus according to the embodiment of the present invention;

FIG. 12 is a table showing an example of permissible error setting data stored in the optometry apparatus according to the embodiment of the present invention;

FIGS. 13A and 13B are schematic views showing examples of axial angle determination process data stored in the optometry apparatus according to the embodiment of the present invention, in which FIG. 13A shows an example of the axial angle determination process data selectively applied when an objective value of astigmatic power of an eye to be examined is −0.25 D to −0.50 D and FIG. 13B shows an example of the axial angle determination process data selectively applied when the objective value of the astigmatic power of the eye to be examined is −0.75 D to −1.25 D;

FIGS. 14A and 14B are schematic views showing examples of axial angle determination process data stored in the optometry apparatus according to the embodiment of the present invention, in which FIG. 14A shows an example of the axial angle determination process data selectively applied when the objective value of the astigmatic power of the eye to be examined is −1.50 D to −2.25 D and FIG. 14B shows an example of the axial angle determination process data selectively applied when the objective value of the astigmatic power of the eye to be examined is −2.50 D to −7.00 D;

DETAILED DESCRIPTION OF THE PREFERRED EMBODIMENT

An example of an optometry apparatus according to a preferred embodiment of the present invention will be described in detail with reference to the accompanying drawings.

Figure 1:
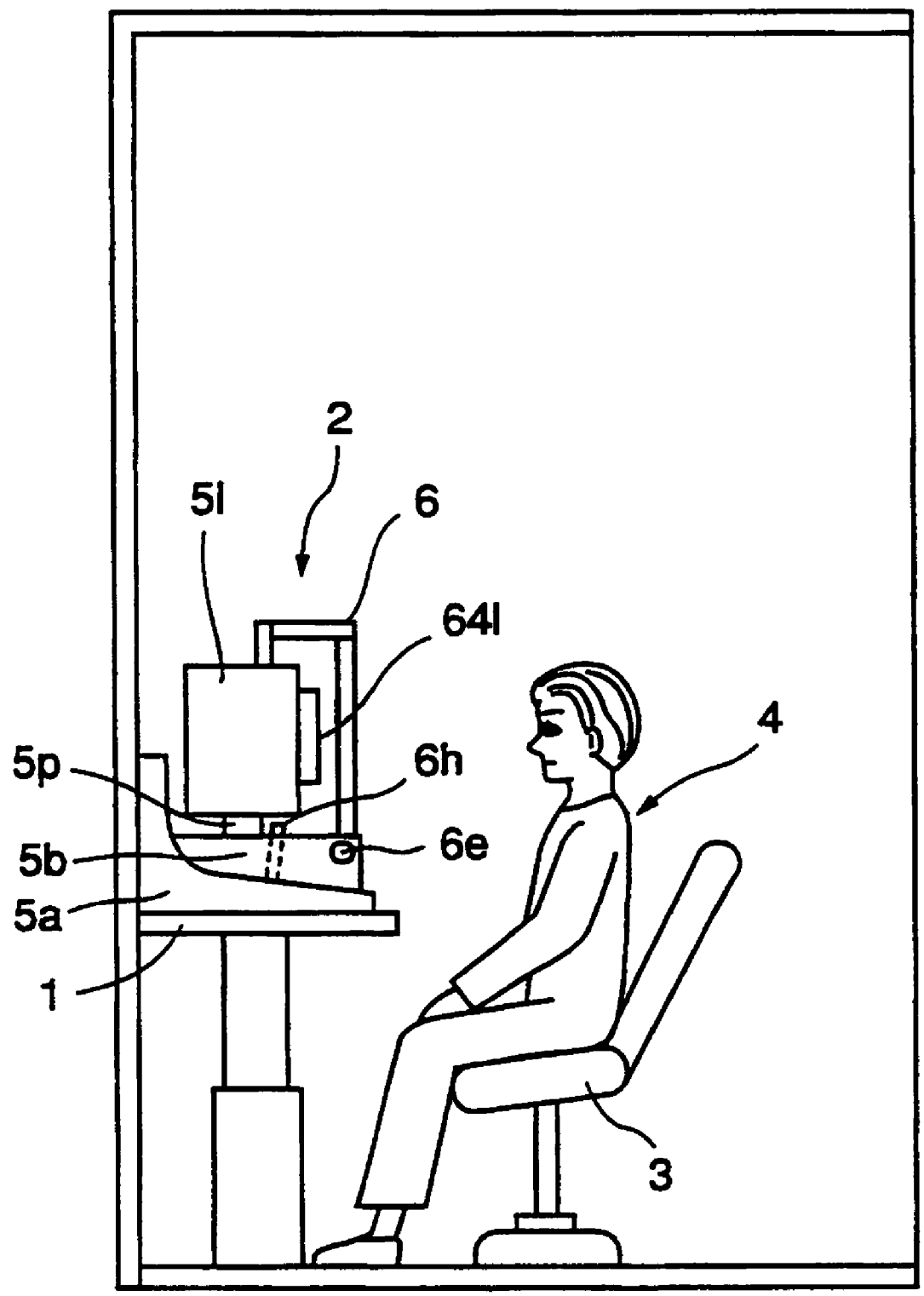
FIG. 1 is a schematic side view showing an example of an external structure of an optometry apparatus according to an embodiment of the present invention.
Figure 2:
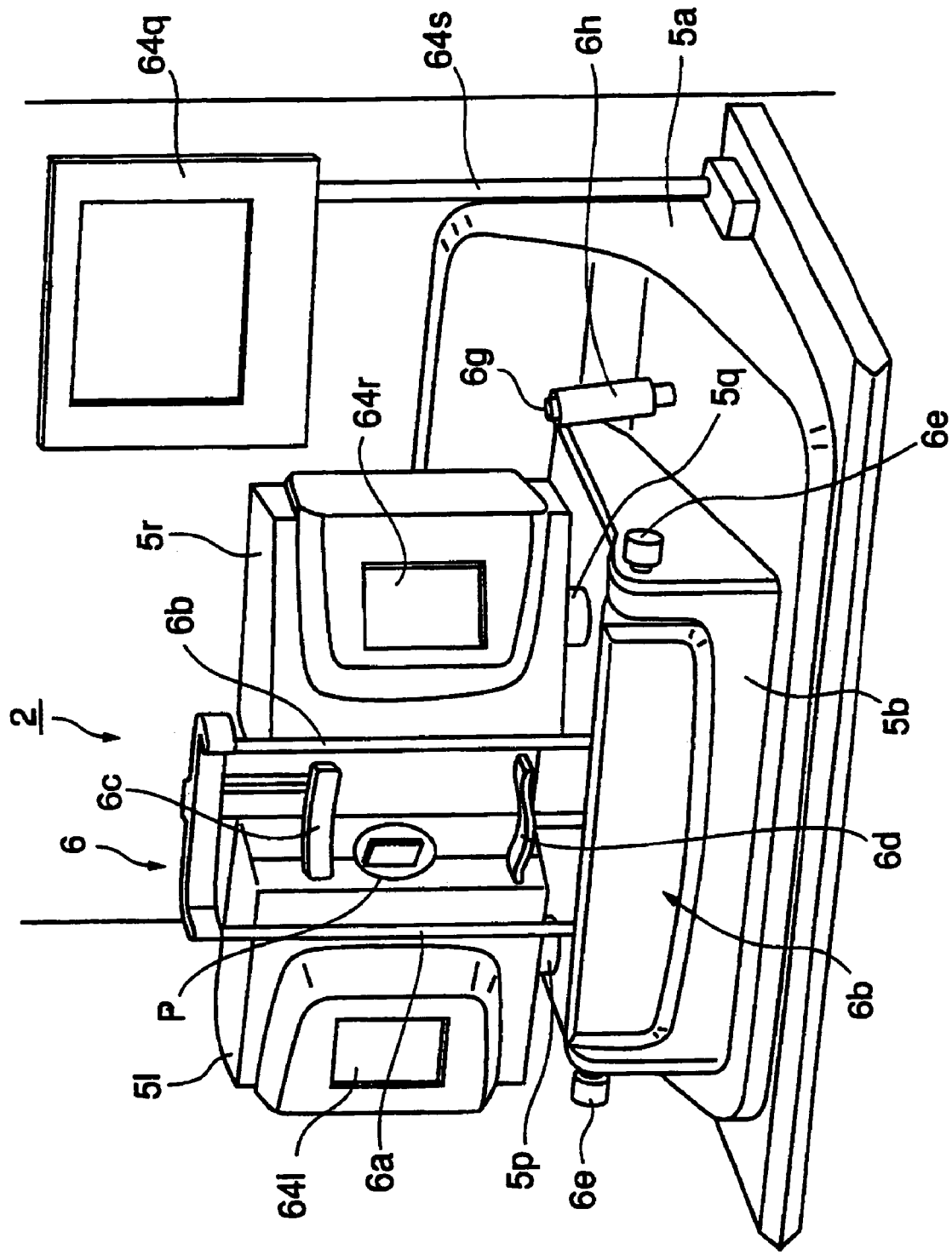
FIG. 2 is a schematic perspective view showing an example of the external structure of the optometry apparatus according to the embodiment of the present invention.
Figure 9:
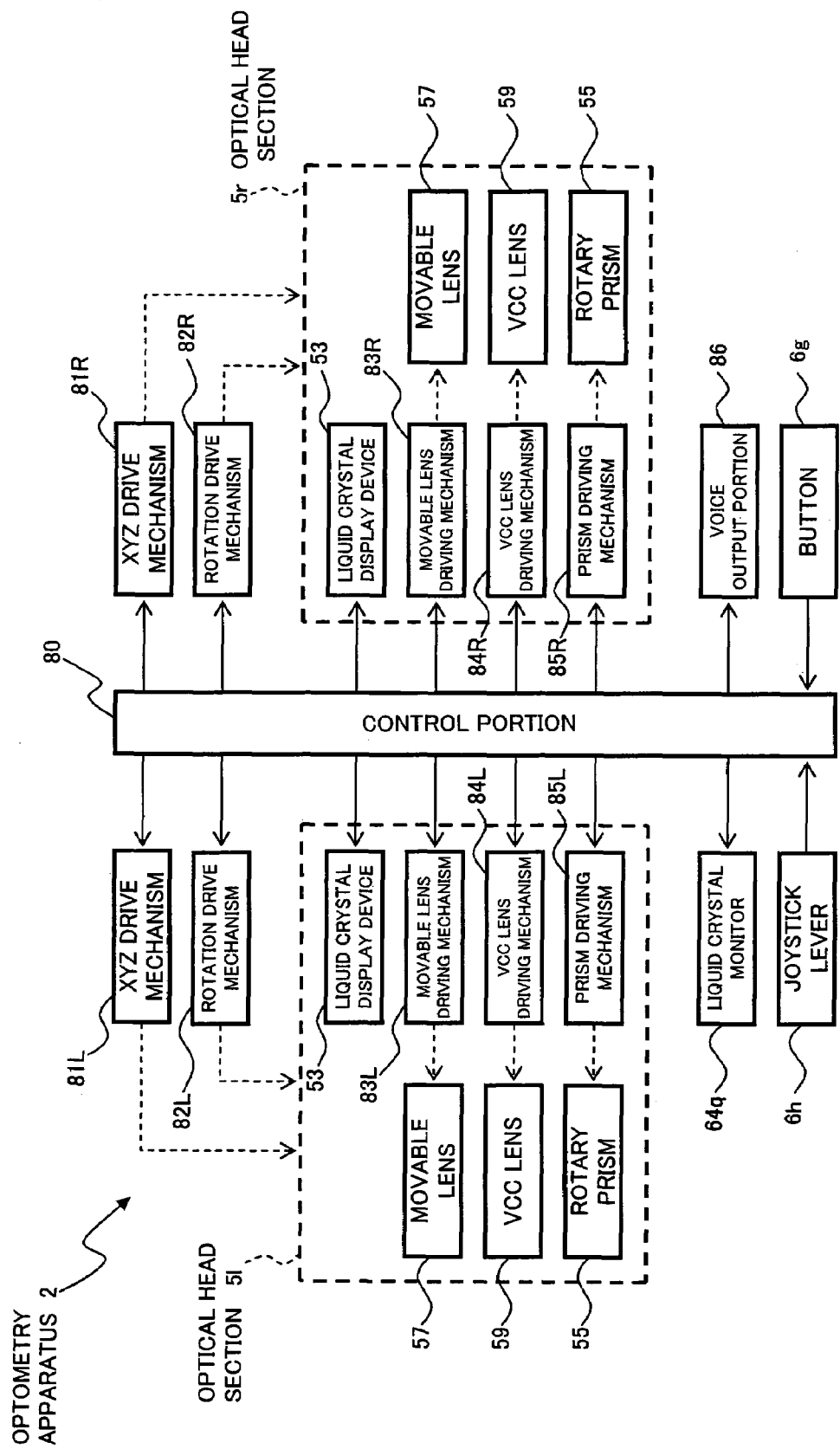
FIG. 9 is a schematic block diagram showing an example of a control system included in the optometry apparatus according to the embodiment of the present invention.
Figure 10:
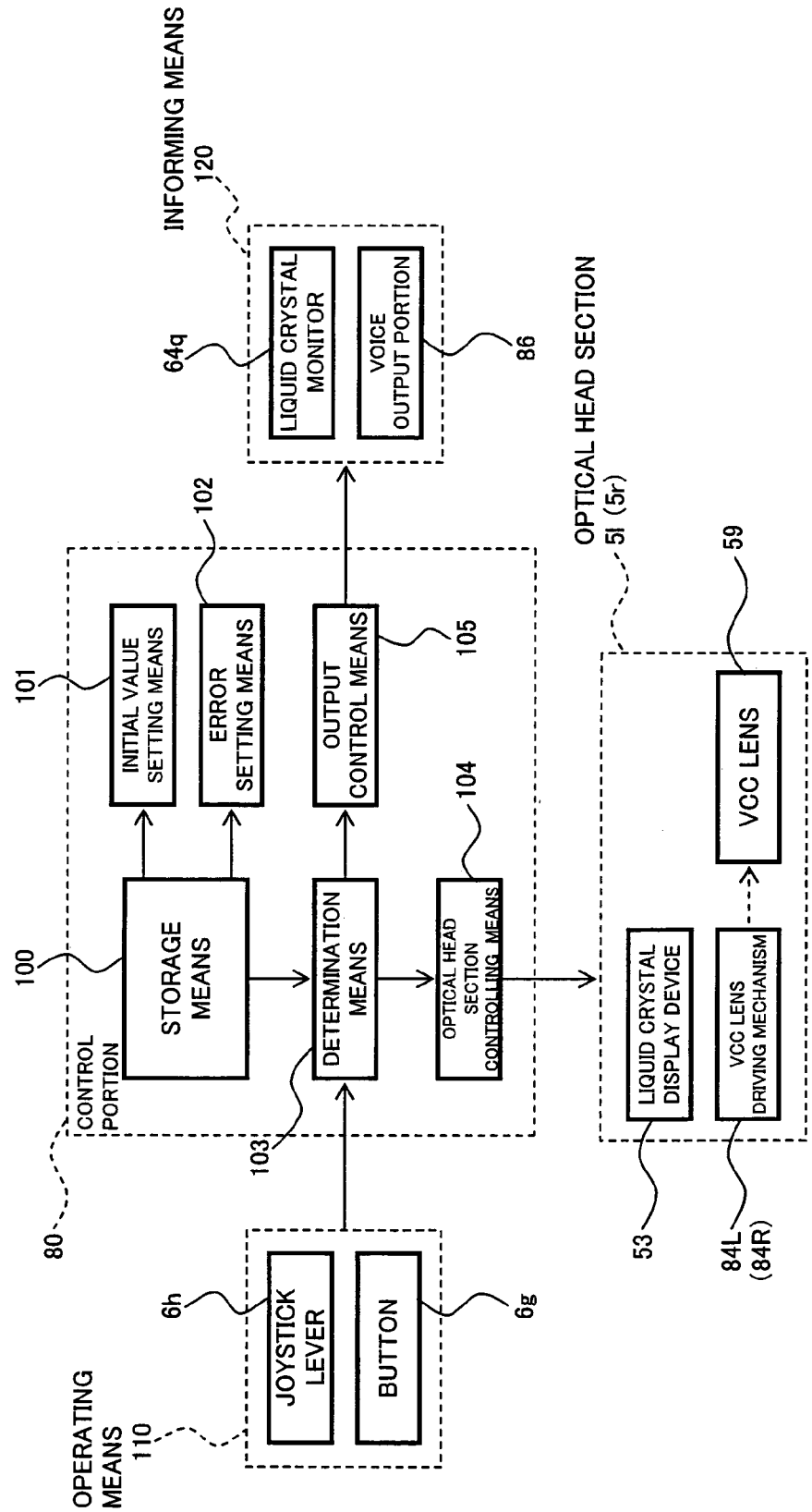
FIG. 10 is a schematic block diagram showing an example of the control system included in the optometry apparatus according to the embodiment of the present invention.
Figure 14A:
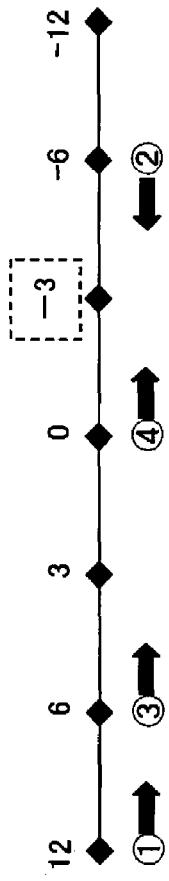
Figure 14B:
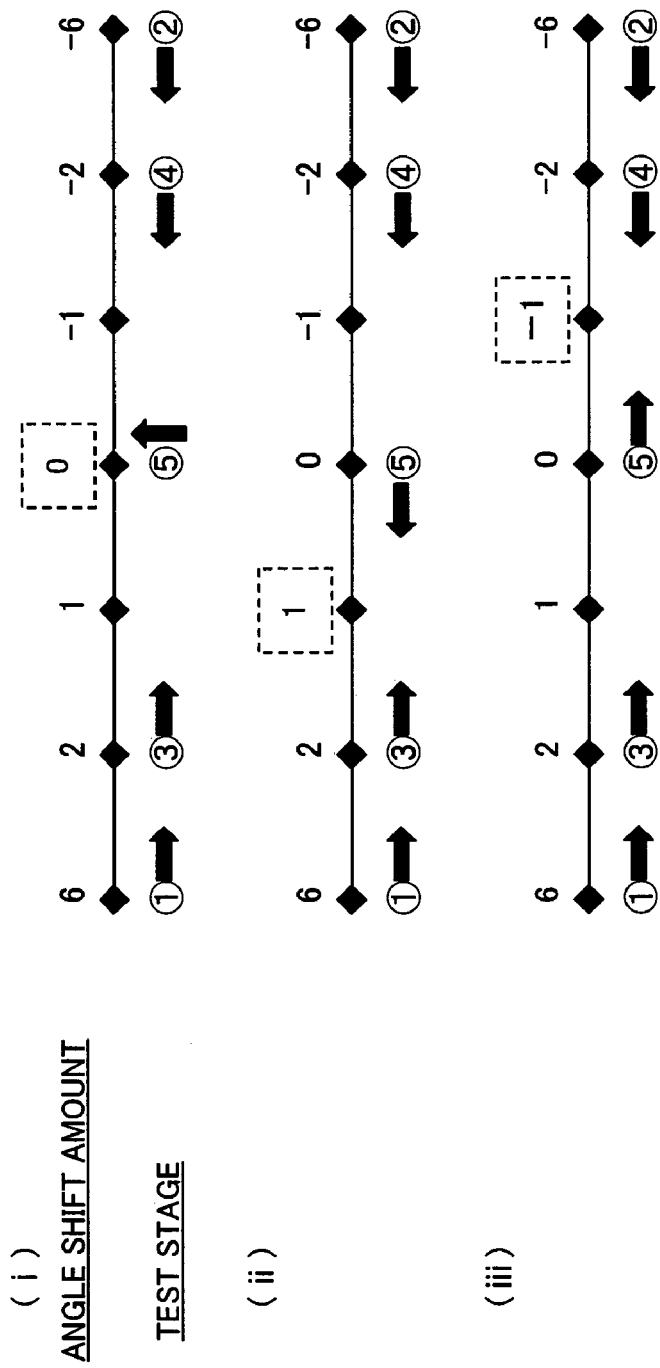
Figure 15:
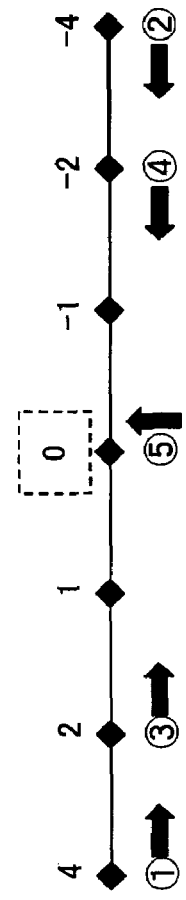
FIG. 15 is a schematic view showing an example of the axial angle determination process data which is stored in the optometry apparatus according to the embodiment of the present invention and selectively applied when the objective value of the astigmatic power of the eye to be examined is −7.25 D to −8.00 D.
Figure 15:
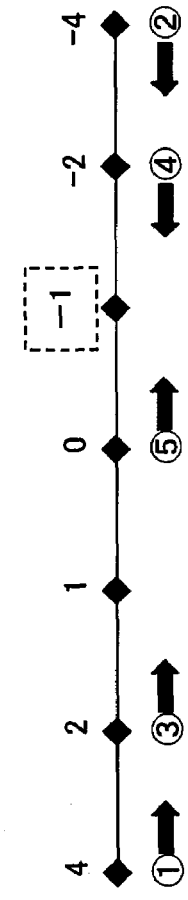
Figure 15:
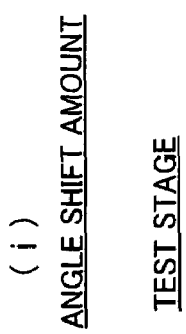
Figure 16:
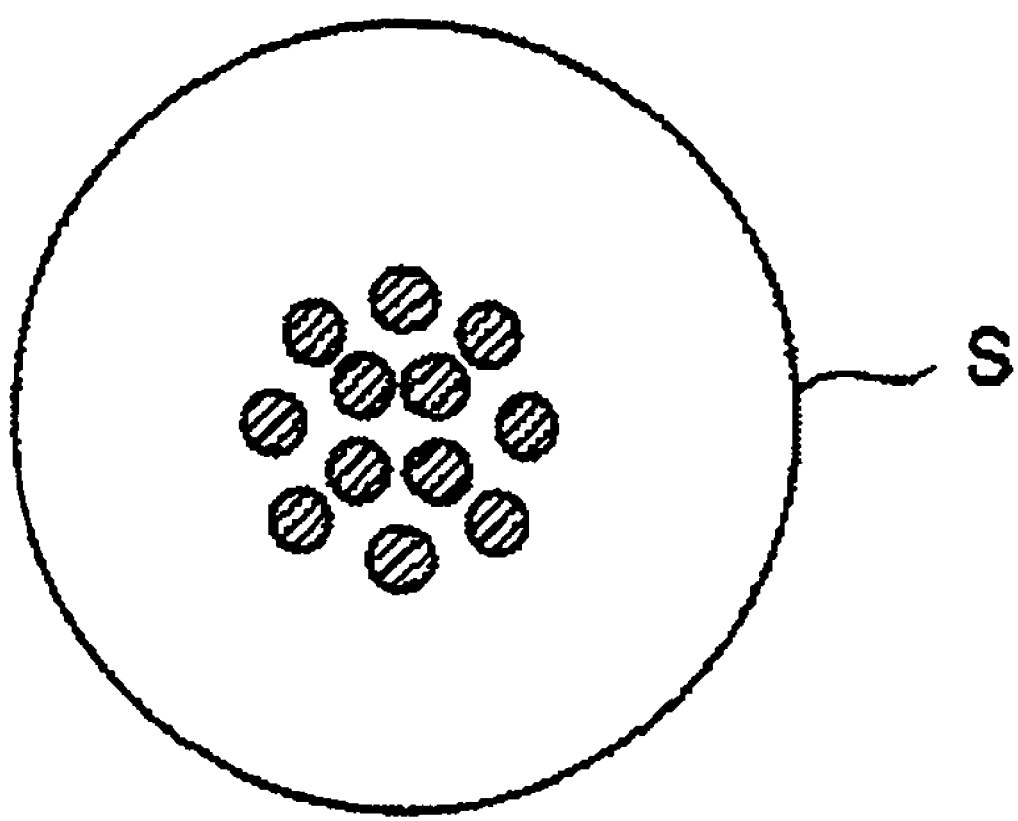
FIG. 16 is a schematic view showing an example of a cross cylinder test chart indicated to the eye to be examined by the measurement optical system included in the optometry apparatus according to the embodiment of the present invention.

FIG. 1 is an external side view showing an optometry apparatus 2 according to this embodiment. FIG. 2 is an external perspective view showing the optometry apparatus. FIGS. 3 to 8 show a structure of an optical system included in the optometry apparatus 2. FIGS. 9 and 10 are block diagrams showing a control system of the optometry apparatus 2. FIGS. 11 to 15 show data used for a cross cylinder test performed by the optometry apparatus 2. FIG. 16 shows a cross cylinder test chart which is an index for cross cylinder test.

[Structure of Apparatus]

As shown in FIG. 1, when in use, the optometry apparatus 2 according to this embodiment is placed on an optometry table 1 whose height is adjustable. A person to be examined 4 performs an examination while seated on an optometry chair 3 provided together with the optometry table 1.

As shown in FIG. 2, a pillar 64s is erected on the optometry table 1. A liquid crystal monitor 64q is provided in an upper end of the pillar 64s.

As shown in FIGS. 1 and 2, the optometry apparatus 2 includes a base portion 5a, a drive mechanism box 5b provided on the base portion 5a, a pair of left and right optical head sections 5l and 5r housing measurement optical systems described later, and a face holding device 6 for holding the face of the person to be examined 4 during an examination. The optical head sections 5l and 5r are respectively supported on pillars 5p and 5q and separately driven in the three-dimensional directions by the drive mechanism box 5b. A liquid crystal monitor 64l is provided on a front surface of the optical head section 5l and a liquid crystal monitor 64r is provided on a front surface of the optical head section 5r. An anterior segment image of the eye to be examined, an eye fundus reflection image thereof, and the like, which are obtained during the examination are displayed on each of the liquid crystal monitors 64l and 64r. An examiner or an assistant can recognize whether or not the examination is properly performed based on the anterior segment image displayed on each of the liquid crystal monitors 64l and 64r.

The face holding device 6 includes a pair of left and right pillars 6a and 6b, a forehead support 6c supported by a member connecting between upper ends of the pillars 6a and 6b, and a chin rest 6d located under the forehead support 6c. The forehead support 6c is a member which is in contact with the forehead of the person to be examined 4 during the examination. The forehead support 6c is formed in an arc shape to improve the contact with the forehead and the position thereof is adjustable in forward and backward directions. The chin rest 6d is a member on which the person to be examined 4 rests the chin during the examination and the position thereof is adjustable in upward and downward directions by a set of right and left knobs 6e. To prepare for the examination, the person to be examined 4 rests the chin on the chin rest 6d and brings the forehead into contact with the forehead support 6c, thus holding the face in position.

The drive mechanism box 5b includes XYZ drive mechanisms for separately driving the optical head sections 5l and 5r supported by the pillars 5p and 5q in the three-dimensional directions. Although the XYZ drive mechanisms are not shown, each of the mechanisms has a known structure using, for example, a pulse motor and a feed screw.

The drive mechanism box 5b further includes a rotation drive mechanism for separately rotating the optical head sections 5l and 5r in the horizontal direction. In the rotation drive mechanism, for example, the torque of a pulse motor is transmitted to the pillars 5p and 5q though gears to rotate the optical head sections 5l and 5r. Then, the optical head sections 5l and 5r are rotated in directions reverse to each other about eyeball rotational points of the right and left eyes of the person to be examined 4.

As shown in FIGS. 3 to 7, each of the optical head sections 5l and 5r houses optical systems. In the optical head sections 5l and 5r, the optical systems are operated to perform objective refraction measurement and subjective refraction measurement on both eyes of the person to be examined 4.

A joystick lever (hereinafter often simply referred to a lever) 6h is provided on the base portion 5a. A button 6g is provided on an upper portion of the lever 6h. The person to be examined 4 suitably operates the lever 6h and the button 6g to perform the examination.

[Structure of Optical System]

Figure 3:
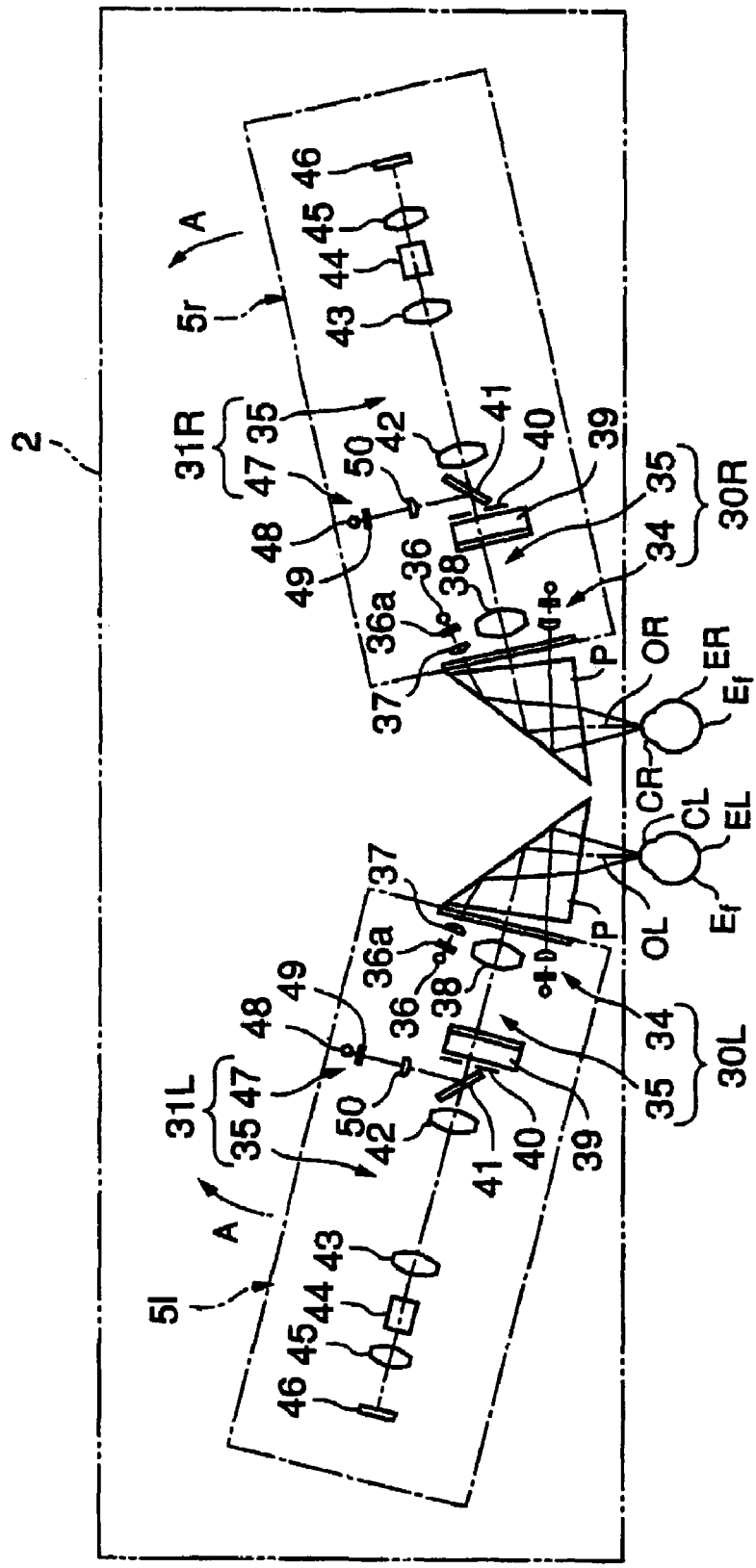
FIG. 3 is a schematic view showing an example of a measurement optical system included in the optometry apparatus according to the embodiment of the present invention.
Figure 4:
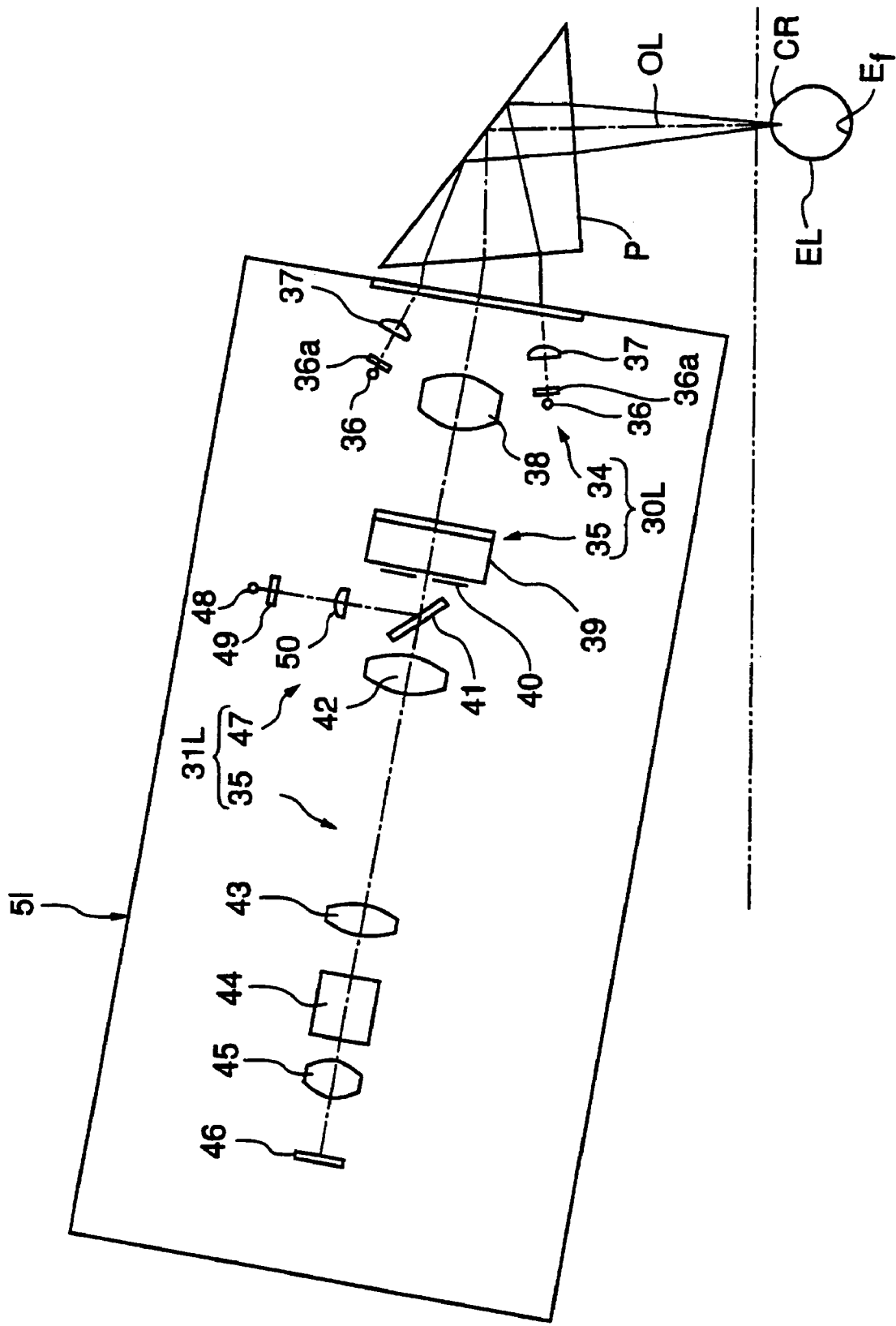
FIG. 4 is a schematic view showing an example of the measurement optical system included in the optometry apparatus according to the embodiment of the present invention.
Figure 5:
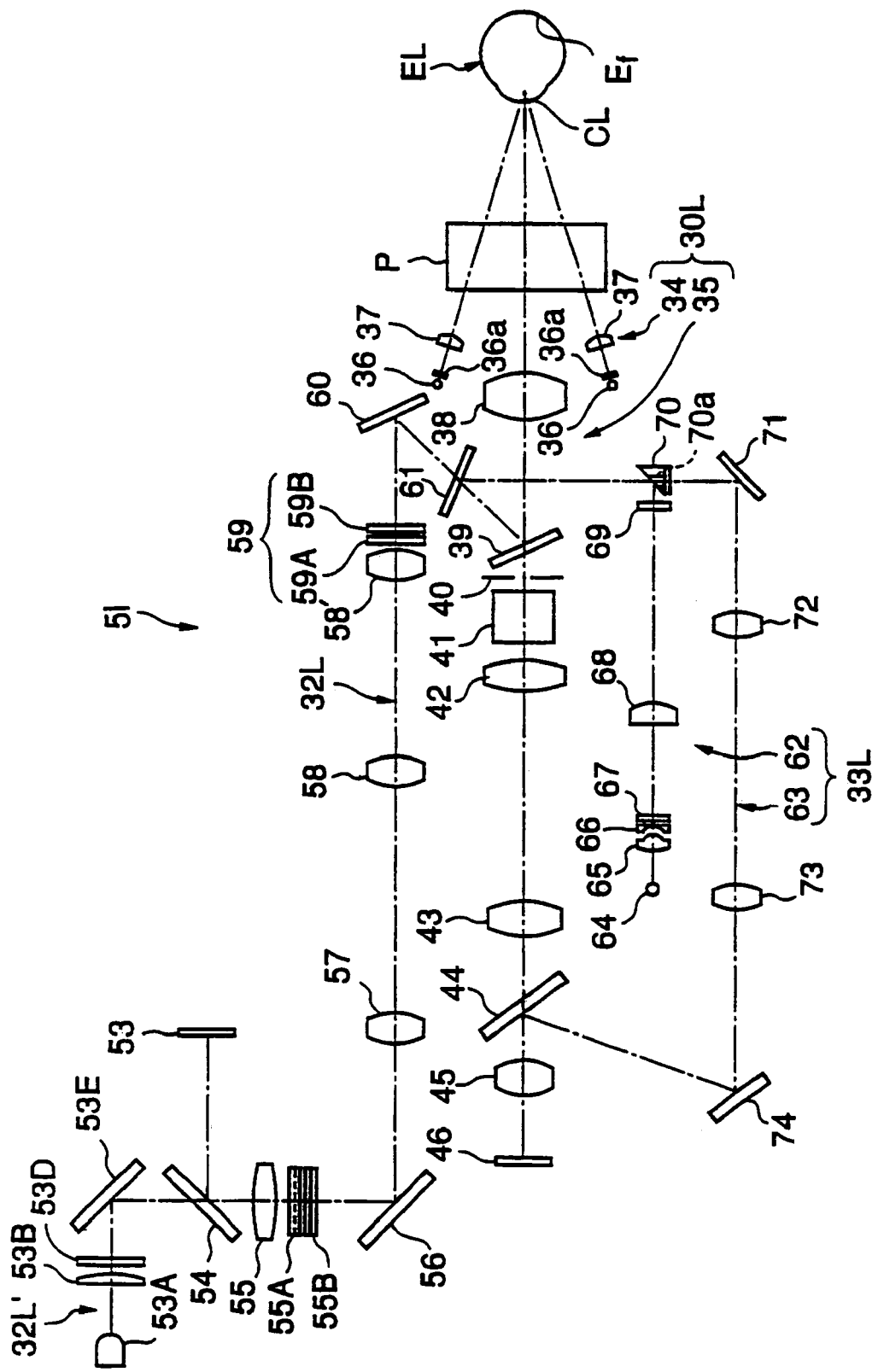
FIG. 5 is a schematic view showing an example of the measurement optical system included in the optometry apparatus according to the embodiment of the present invention.
Figure 6:
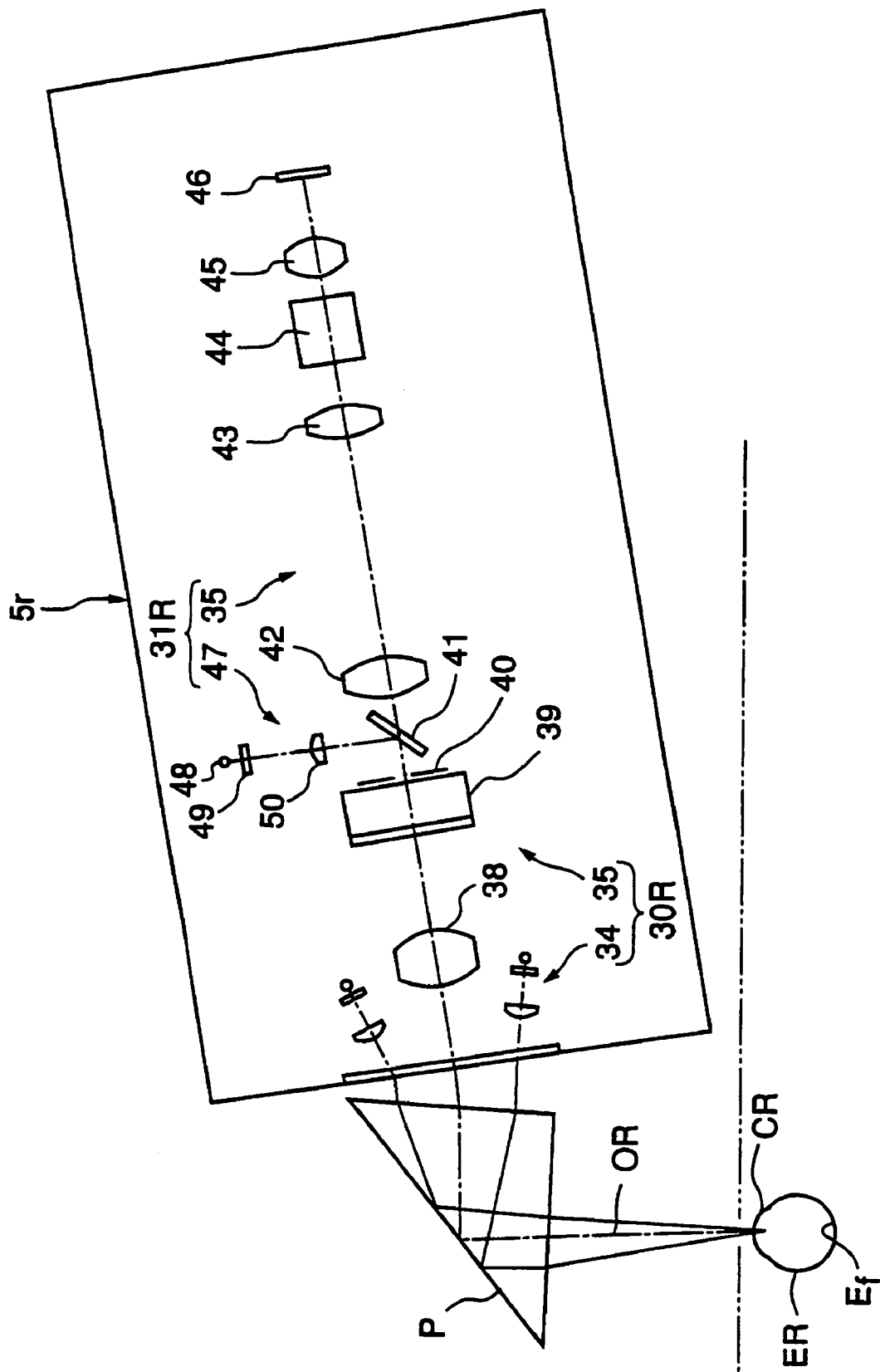
FIG. 6 is a schematic view showing an example of the measurement optical system included in the optometry apparatus according to the embodiment of the present invention.
Figure 7:
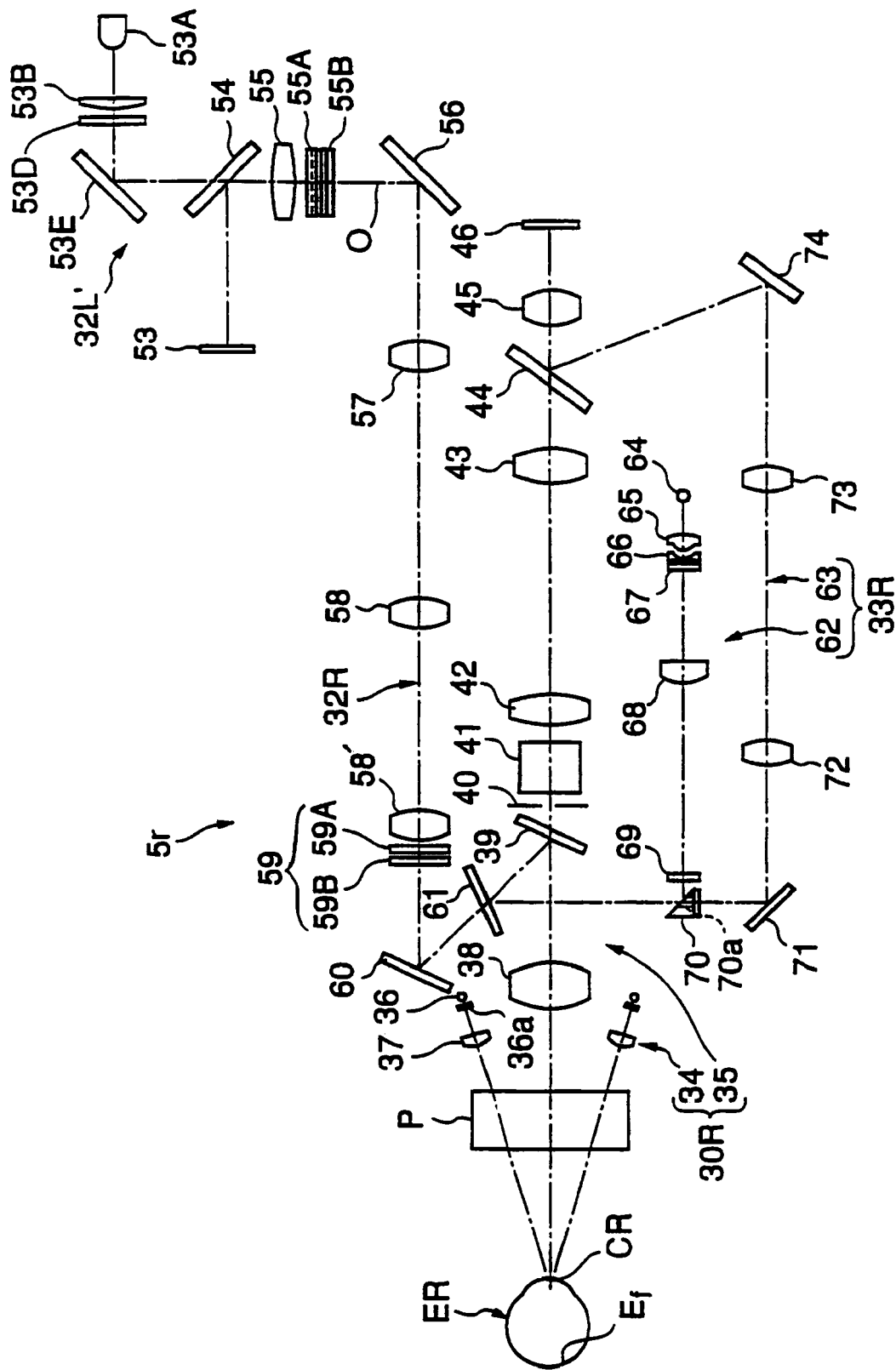
FIG. 7 is a schematic view showing an example of the measurement optical system included in the optometry apparatus according to the embodiment of the present invention.

Structures of measurement optical systems housed in the optical head sections 5l and 5r will be described in detail. First, as shown in FIGS. 3 to 5, the optical head section 5l for measuring the left eye of the person to be examined 4 includes an anterior segment image taking optical system 30L, an XY-alignment optical system 31L, an index projecting optical system 32L, and a refractive power measuring optical system 33L. As shown in FIGS. 3, 6, and 7, the optical head section 5r for measuring the right eye of the person to be examined 4 includes an anterior segment image taking optical system 30R, an XY-alignment optical system 31R, an index projecting optical system 32R, and a refractive power measuring optical system 33R. The measurement optical system of the optical head section 5l and the measurement optical system of the optical head section 5r are symmetrically disposed. Hereinbelow, unless otherwise specified, the measurement optical system of the optical head section 5l for measuring the left eye will be described.

The anterior segment image taking optical system 30L provided in the optical head section 5l includes an anterior segment illuminating optical system 34 and an image taking optical system 35.

As shown in FIGS. 4, and 5, the anterior segment illuminating optical system 34 includes light sources 36 for illuminating the anterior segment of the left eye of the person to be examined 4 (eye to be examined EL), diaphragms 36a for limiting cross sectional areas of light fluxes emitted from the light sources 36, and projection lenses 37 for projecting the light fluxes passing through the diaphragms 36a to the anterior segment of the eye to be examined EL.

The image taking optical system 35 includes a prism P, an objective lens 38, a dichroic mirror 39, a diaphragm 40, a dichroic mirror 41, relay lenses 42 and 43, a dichroic mirror 44, a CCD 46, and a CCD lens 45 for imaging a light flux on a light receiving surface of the CCD 46. Reflection light on the anterior segment of the eye to be examined EL which is illuminated by the anterior segment illumination optical system 34 is incident on the prism P. A light flux reflected on a reflective surface of the prism P is incident on the objective lens 38.

The XY-alignment optical system 31L is an optical system for aligning the measurement optical system of the optical head section 5l with the eye to be examined EL in X- and Y-directions. The XY-alignment optical system 31L includes an alignment illumination optical system 47 for projecting an alignment light flux to the eye to be examined EL and the image taking optical system 35 for receiving reflection light on the eye to be examined EL, serving as an alignment light receiving optical system. Assume that the right-and-left direction as viewed from the person to be examined 4 is an X-direction and the up-and-down direction as viewed from the person to be examined 4 is a Y-direction. In addition, assume that the depth direction of the optometry apparatus 2 as viewed from the person to be examined 4 is a Z-direction.

As shown in FIGS. 3 and 4, the alignment illumination optical system 47 includes an illumination light source 48 for emitting a light flux for alignment in the X- and Y-directions, a diaphragm 49 as an alignment index, a relay lens 50, the dichroic mirror 41, the diaphragm 40, the dichroic mirror 39, the objective lens 38, and the prism P.

The index projecting optical system 32L includes a liquid crystal display device 53 for displaying various indexes (charts) for eye examination, a half mirror 54 for reflecting light from the liquid crystal display device 53, a collimator lens 55, rotary prisms 55A and 55B for adjusting prism power and a prism base direction in a phoria examination, and a reflective mirror 56. The index projecting optical system 32L further includes a movable lens 57 used to perform, for example, fixation and fogging on the eye to be examined EL, relay lenses 58 and 58', variable cross cylinder lenses (VCC lenses) 59 for adjusting astigmatic power of the eye to be examined EL and an astigmatic axial angle thereof in a cross cylinder test, a reflective mirror 60, a dichroic mirror 61, the dichroic mirror 39, the objective lens 38, and the prism P.

The liquid crystal display device 53 selectively displays a fixed index including a scene chart and various indexes such as a visual acuity chart including Landolt rings for visual acuity examination, a cross cylinder test chart S (see FIG. 16), a fan chart for astigmatic examination, a cross chart for phoria examination, and a red-green test chart. Note that a known index indicating means for illuminating a turret plate having a plurality of indexes from behind to indicate the indexes may be used instead of the liquid crystal display device 53.

The rotary prisms 55A and 55B are separately driven to be rotated by a pulse motor or the like. When the rotary prisms 55A and 55B rotate in directions reverse to each other, the prism power continuously changes. On the other hand, when the rotary prisms 55A and 55B integrally rotate in the same direction, the prism base direction continuously changes.

Figure 8:
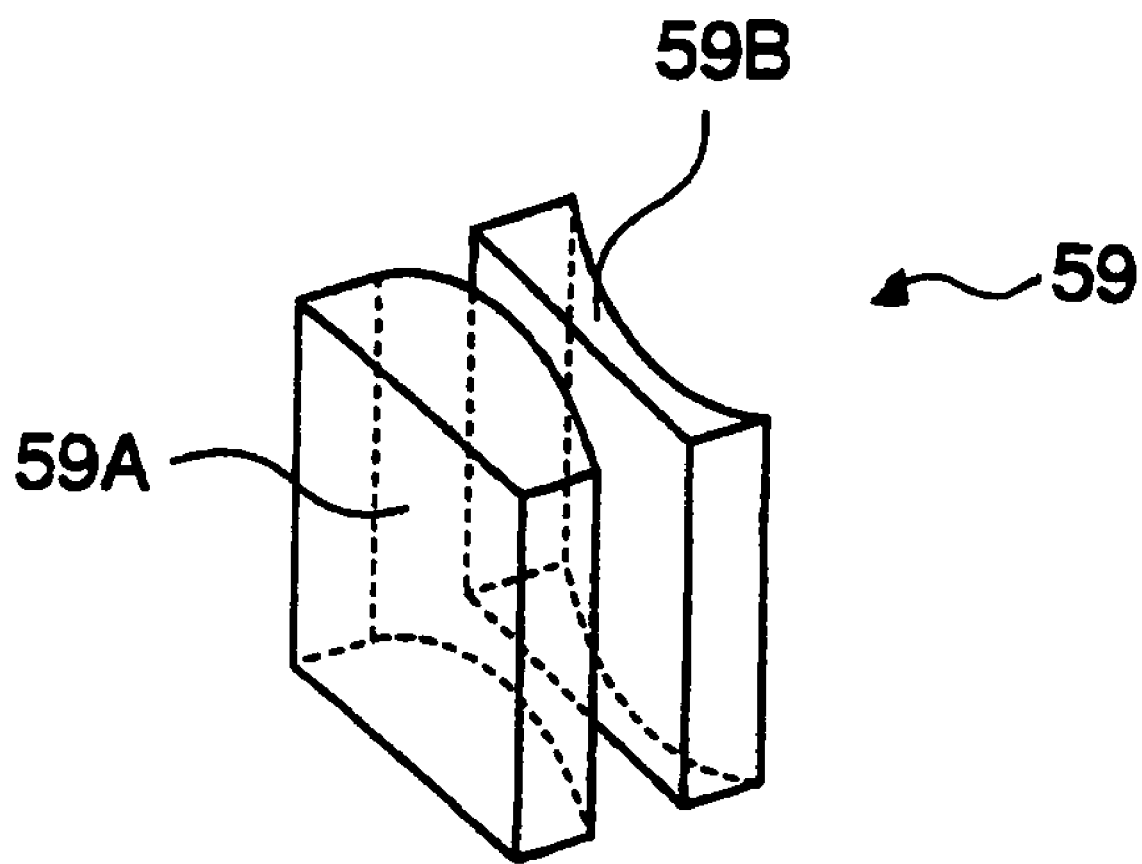
FIG. 8 is a schematic perspective view showing an example of a variable cross cylinder lens of the measurement optical system included in the optometry apparatus according to the embodiment of the present invention.

As shown in FIG. 8, the VCC lens 59 includes a cylindrical lens 59A having a convex surface (positive power) and a cylindrical lens 59B having a concave surface (negative power). The cylindrical lenses 59A and 59B are separately rotated about the optical axis of the index projecting optical system 32L by a drive device such as a pulse motor. When cylindrical lenses 59A and 59B rotate in directions reverse to each other, astigmatic power changes. On the other hand, when the cylindrical lenses 59A and 59B integrally rotate in the same direction, an astigmatic axial angle changes.

In particular, in each stage of the cross cylinder test, the astigmatic axial angle is reversed (axial direction associated with positive power and axial direction associated with negative power are adjusted) by the VCC lens 59 while predetermined astigmatic power is set, thereby forming a pair of projection images of the cross cylinder test chart S (see FIG. 16). The pair of projection images is projected to the eyes to be examined EL and ER while the images are alternately switched therebetween. The person to be examined compares appearance states of the pair of projection images with each other and operates the lever 6h or the like to perform a response input as to which of the projection images can be more clearly visually recognized.

The movable lens 57 is moved in the optical axis direction of the index projecting optical system 32L by a drive device such as a pulse motor to change spherical power added to the eye to be examined EL. For example, the movable lens 57 is moved in the optical axis direction by a distance corresponding to the refractive power of the eye to be examined EL to perform the fixation and fogging on the eye to be examined EL.

As shown in FIG. 5, a fusion index projecting optical system 32L' is provided in a passing-through direction of the half mirror 54 of the index projecting optical system 32L. The fusion index projecting optical system 32L' includes an LED 53A for emitting illumination light, a collimator lens 53B, a fusion frame chart 53D, and a total reflection mirror 53E. The fusion frame chart 53D has, for example, a light shielding member in which a square transmission window (fusion window) is formed. The collimator lens 53B has a diffusing surface for diffusing light from the LED 53A to uniformly illuminate the fusion frame chart 53D with the diffused light.

In this embodiment, the fusion index projecting optical system 32L' is provided separate from the index projecting optical system 32L. However, the fusion frame may be displayed on the liquid crystal display device 53.

As shown in FIG. 5, the refractive power measuring optical system 33L includes a measurement light flux projecting optical system 62 for projecting a light flux for objective measurement to the eye to be examined EL and a measurement light flux receiving optical system 63 for receiving reflection light of the projected light flux on the eye to be examined EL.

The measurement light flux projecting optical system 62 includes a measurement light source 64 such as an infrared LED, a collimator lens 65, a cone prism 66, a ring index 67, a relay lens 68, a ring diaphragm 69, a holed prism 70 in which a transmission hole 70a is formed at the center, the dichroic mirrors 61 and 39, the objective lens 38, and the prism P.

The measurement light flux receiving optical system 63 includes the prism P on which reflection light on an eye fundus Ef of the eye to be examined EL is incident, the objective lens 38, the dichroic mirrors 39 and 61, the holed prism 70 having the transmission hole 70a, a reflective mirror 71, a relay lens 72, a movable lens 73, a reflective mirror 74, the dichroic mirror 44, the CCD lens 45, and the CCD 46.

The optometry apparatus 2 according to this embodiment automatically executes an alignment of the optical systems of the optical head sections 5l and 5r with the eyes to be examined EL and ER, objective optometry measurement, subjective optometry measurement, a binocular balance test, or the like under the control of a control system described later. Values determined by the objective optometry measurement (objective values) are used for the subjective optometry measurement. In particular, the astigmatic power and the astigmatic axial angle which are determined by the objective optometry measurement are used for the cross cylinder test of the subjective optometry measurement.

[Structure of Control System and Processing Content]

Next, a structure of a control system of the optometry apparatus 2 according to this embodiment and the contents of processing in this embodiment will be described with reference to FIGS. 9 to 15. FIG. 9 is a block diagram showing a schematic structure of a main part of the control system of the optometry apparatus 2. FIG. 10 is a block diagram showing a schematic structure of a part of the control system which executes processing according to the present invention. FIGS. 11 to 15 show cross cylinder test data used to execute the cross cylinder test.

As shown in FIG. 9, the control system of the optometry apparatus 2 includes a control portion 80 for controlling respective parts of the apparatus, serving as a main component. The control portion 80 is housed in, for example, the base portion 5a of the optometry apparatus 2 and includes a nonvolatile storage device such as a ROM and an arithmetic and control device such as CPU. The nonvolatile storage device stores a computer program for eye examination, including a control program for processing as described later. The arithmetic and control device executes the computer program. In particular, the control portion 80 corresponds to a "control means" for performing various controls during the cross cylinder test.

The optometry apparatus 2 is connected to a computer apparatus (not shown). The computer apparatus is used as a console of the optometry apparatus 2. The computer apparatus is also used to store and manage results obtained by the examination using the optometry apparatus 2. A CPU and a storage device of the computer apparatus can be used for the control portion 80.

The control portion 80 controls the operation of each of the optical head section 5l and 5r. More specifically, the control portion 80 controls an XYZ drive mechanism 81L for three-dimensionally driving the left optical head section 5l in the X-, Y-, and Z-directions and a rotation drive mechanism 82L for rotating the optical head section 5l in the horizontal direction. Similarly, the control portion 80 controls an XYZ drive mechanism 81R for three-dimensionally driving the right optical head section 5r in the X-, Y-, and Z-directions and a rotation drive mechanism 82R for rotating the optical head section 5r in the horizontal direction.

The control portion 80 controls the operations of the optical systems housed in the optical head section 5l and 5r. For example, the control portion 80 executes the display controls of the liquid crystal display devices 53, the operational controls of movable lens driving mechanisms 83L and 83R for driving the movable lenses 57 in the optical axis direction, the operational controls of VCC lens driving mechanisms 84L and 84R for rotating the VCC lenses 59 about the optical axes of the index projecting optical system 32L and 32R, and the operational controls of prism driving mechanisms 85L and 85R for rotating the rotary prisms 55A and 55B about the optical axis.

The control portion 80 also performs the display control of the liquid crystal monitor 64q (see FIG. 2), the output control of a voice output portion 86. The voice output portion 86 outputs voice information such as voice navigation information for automatically advancing the eye examination.

In addition to the above-mentioned controls, the control portion 80 executes all operational controls of the optometry apparatus 2, including the turning on/off control of each of the light sources 36, the illumination light source 48, the LED 53A, and the like. The control portion 80 also executes all data processings in the optometry apparatus 2, including image processing on an image picked up by the CCD 46.

FIG. 10 is a detailed block diagram showing a part of the control system shown in FIG. 9, which shows a structure for executing characteristic processing of the present invention. The joystick lever 6h and the button 6g compose an operating means 110 operated to input a result obtained by comparison between the appearance states of the pair of projection images of the cross cylinder test chart S.

The control portion 80 includes a storage means 100, an initial value setting means 101, an error setting means 102, a determination means 103, an optical head section controlling means 104, and an output control means 105.

The operations of the initial value setting means 101, the error setting means 102, and the determination means 103 will be described later. The optical head section controlling means 104 controls the respective parts (particularly, the liquid crystal display devices 53 and the VCC lens driving mechanisms 84L and 84R) of the optical head sections 5l and 5r. The output control means 105 controls, for example, a display output to the liquid crystal display device 64q, a voice output to the voice output portion 86, and display outputs to the liquid crystal monitors 64l and 64r.

The storage means 100 is a nonvolatile storage device such as a ROM and prestores, for example, results obtained by examination on the eyes to be examined EL and ER (particularly, objective values of astigmatic powers and astigmatic axial angles), various optometry data including cross cylinder test data shown in FIGS. 11 to 15, and optometry control programs.

The cross cylinder test data shown in FIG. 11 is information referred to in order to set an astigmatic axial angle value (initial value) applied at a first stage of the cross cylinder test performed on the eyes to be examined EL and ER. Hereinafter, the data is referred to as initial value setting data.

The initial value setting data includes the objective values of the astigmatic powers and angle shift amounts which are associated therewith and set based on the objective value of the astigmatic axial angle. More specifically, when the objective value of the astigmatic power is −0.25 diopters (D), the angle shift amount is set to 40°. When the objective value of the astigmatic power is −0.50 D, the angle shift amount is set to 30°. When the objective value of the astigmatic power is −0.75 D to −1.00 D, the angle shift amount is set to 25°. When the objective value of the astigmatic power is −1.25 D, the angle shift amount is set to 20°. When the objective value of the astigmatic power is −1.50 D to −2.00 D, the angle shift amount is set to 15°. When the objective value of the astigmatic power is −2.25 D to −3.75 D, the angle shift amount is set to 10°. When the objective value of the astigmatic power is −4.00 D to −7.00 D, the angle shift amount is set to 5°. When the objective value of the astigmatic power is −7.25 D to −8.00 D, the angle shift amount is set to 3°.

The angle shift amounts for the respective astigmatic powers, which are defined in the initial value setting data shown in FIG. 11 are set to such values that one of the pair of projection images of the cross cylinder test chart S is clearly visually recognized and the other thereof is visually recognized with a blurred state. For example, in the case of weak astigmatism in which the astigmatic power is −0.25 D, when an angle is shifted from the astigmatic axial angle of the eye to be examined by about 40°, the one projection image is clearly visually recognized and the other projection image is visually recognized with the blurred state. In the case of strong astigmatism in which the astigmatic power is −8.00 D, even when the angle is shifted from the astigmatic axial angle of the eye to be examined by about 3°, the one projection image is clearly visually recognized and the other projection image is visually recognized with the blurred state. Note that the recent objective eye examination has high measurement precision and the true astigmatic axial angle of the eye to be examined is unknown before the cross cylinder test. In this embodiment, the angle shift amount from the objective value of the astigmatic axial angle is used to set the initial value in view of the circumstances mentioned above.

Hereinafter, the initial-value setting processing for the cross cylinder test using the initial value setting data will be described. The initial-value setting processing is executed by the initial value setting means 101 of the control portion 80. The initial value setting means 101 determines, from the initial value setting data shown in FIG. 11, the amount of shift of the astigmatic axial angle which is associated with the objective value of the astigmatic power of each of the eyes to be examined EL and ER which is measured in advance. An angle in which the objective value of the astigmatic axial angle of each of the eyes to be examined EL and ER is shifted by the determined angle shift amount is set as the initial value for the cross cylinder test.

For example, assume that the objective value of the astigmatic power of the eye to be examined is −0.25 D and the objective value of the astigmatic axial angle thereof is 30°. In this case, when the initial value setting data is referred to, the angle shift amount corresponding to the objective value of the astigmatic axial angle is 40°. Therefore, the objective value of the astigmatic axial angle of 30° is shifted by the angle shift amount of 40°, and an angle of 70° is obtained. The angle of 70° is set as the initial value for the cross cylinder test.

The cross cylinder test data shown in FIG. 12 is information referred to set an error allowable (permissible error) for the cross cylinder test performed on the eyes to be examined EL and ER, that is, an allowable measurement error range for astigmatic axial angle measurement. Hereinafter, the data is referred to as permissible error setting data.

The permissible error setting data includes the objective values of the astigmatic powers and permissible errors for the astigmatic axial angle measurement which are associated therewith. More specifically, when the objective value of the astigmatic power is −0.25 D, the permissible error is set to 15°. When the objective value of the astigmatic power is −0.50 D, the permissible error is set to 10°. When the objective value of the astigmatic power is −0.75 D to −1.25 D, the permissible error is set to 5°. When the objective value of the astigmatic power is −1.50 D to −2.25 D, the permissible error is set to 3°. When the objective value of the astigmatic power is −2.50 D to −8.00 D, the permissible error is set to 1°.

The permissible errors for the respective astigmatic powers, which are defined in the permissible error setting data shown in FIG. 12 are set in error ranges in which the astigmatic axial angles associated with the objective values of the astigmatic powers may be able to be measured with sufficient precision. To explain it in more detail, the permissible error values are set so as to satisfy the following two conditions. (Condition 1) When objective values of astigmatic power and an astigmatic axial angle of each of the eyes to be examined EL and ER are corrected by a corrective lens and then the astigmatic axial angle is shifted, residual astigmatism is caused. The residual astigmatism is within −0.25 D (first predetermined range). (Condition 2) When the objective values of the astigmatic power and the astigmatic axial angle are combined with the astigmatic power of the corrective lens and the astigmatic axial angle thereof, respectively, spherical power changes. The amount of change in spherical power becomes smaller than −0.25 D (second predetermined range). Note that the first predetermined range and the second predetermined range can be set as appropriate. The permissible error satisfying the above-mentioned Conditions 1 and 2 may be set as a permissible error suitable for the objective value of the astigmatic power, that is, a permissible error in which measurement precision is neither too high nor too low.

Hereinafter, the permissible error setting processing for the cross cylinder test using the permissible error setting data will be described. The permissible error setting processing is executed by the error setting means 102 of the control portion 80. The error setting means 102 determines, from the permissible error setting data shown in FIG. 12, the permissible error which is associated with the objective value of the astigmatic power of each of the eyes to be examined EL and ER which is measured in advance. The determined permissible error is set as the permissible error for the astigmatic axial angle measurement of each of the eyes to be examined EL and ER.

For example, assume that the objective value of the astigmatic power of the eye to be examined is −0.25 D. In this case, when the permissible error setting data is referred to, the permissible error for the objective value of the astigmatic axial angle is 15°. Therefore, the angle of 15° is set as the permissible error for the astigmatic axial angle measurement performed during the cross cylinder test. The astigmatic axial angle measurement is performed on the eye to be examined with such a precision that a final measurement value is within the permissible error.

Next, the cross cylinder test data shown in FIGS. 13A to 15 will be described. The data shown in each of FIGS. 13A, 13B, 14A, 14B, and 15 schematically shows a process for determining the astigmatic axial angle based on the objective value of the astigmatic power. Hereinafter, the data is referred to as axial angle determination process data (may be abbreviated to process data). The process data shows a process for determining a final astigmatic axial angle by the optimization of the astigmatic axial angle of each of the eyes to be examined EL and ER by changing the astigmatic axial angle of the VCC lens 59 to any value in any order.

Figure 13A:
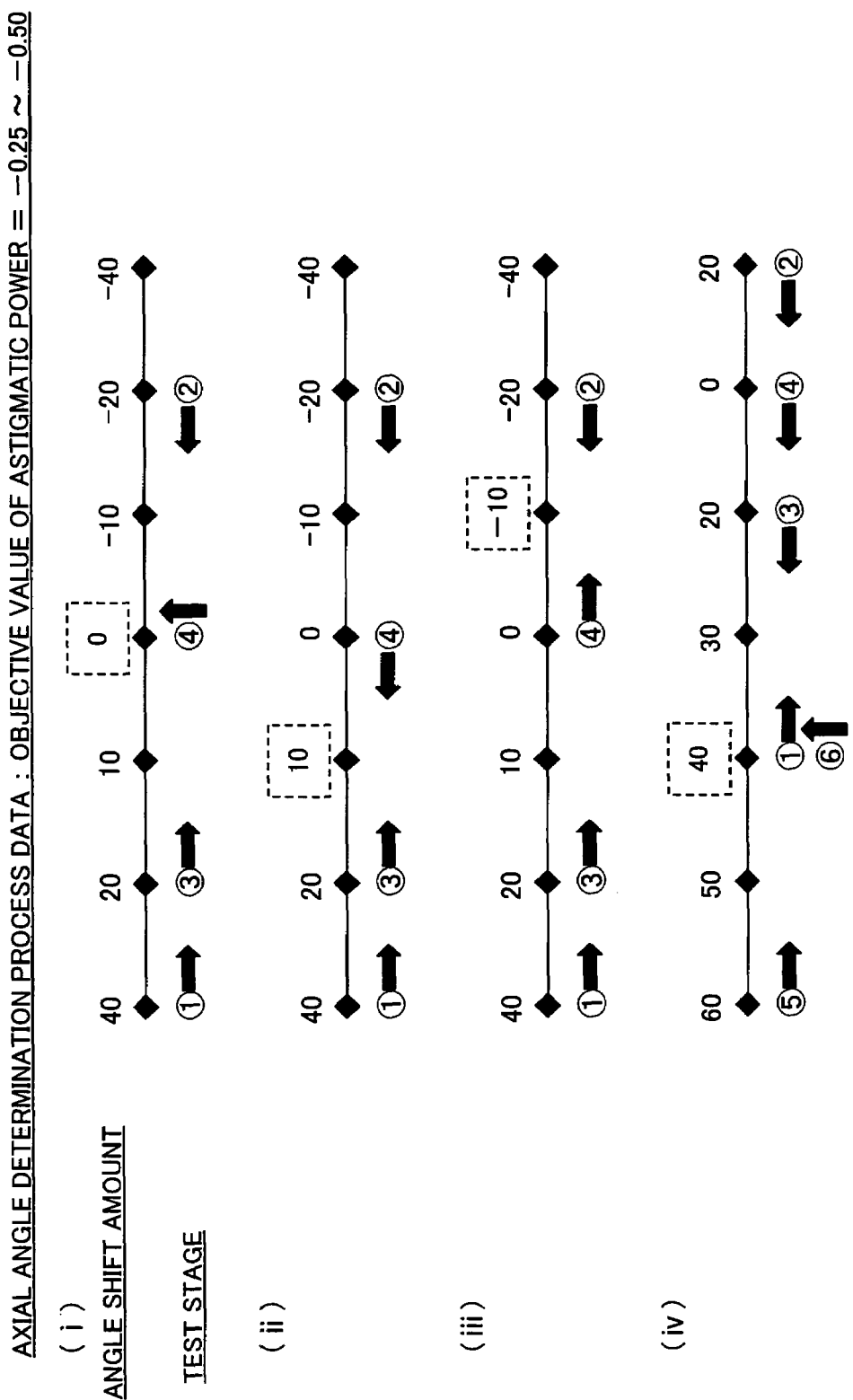
Figure 13B:
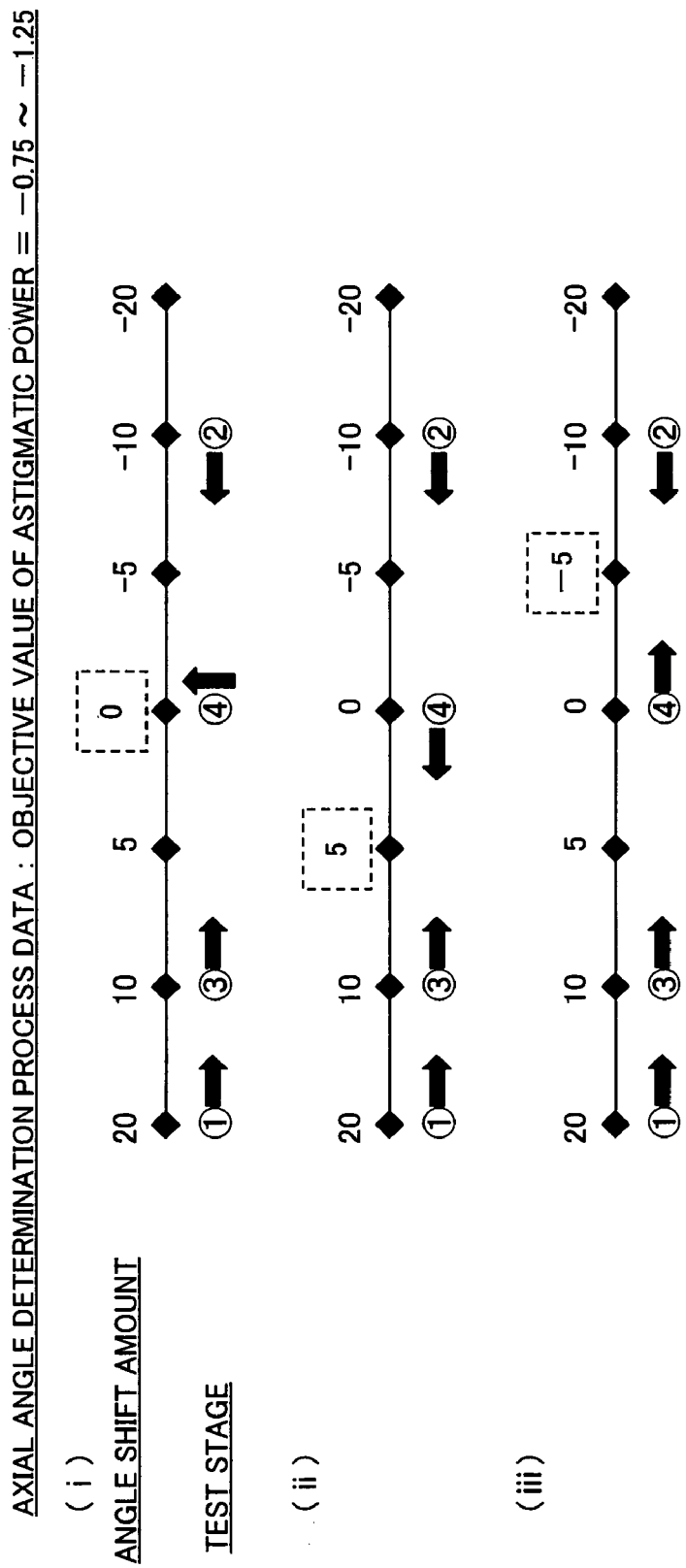

The process data shown in FIG. 13A is selectively applied when the objective value of the astigmatic power is −0.25 D to −0.50 D. The process data shown in FIG. 13B is selectively applied when the objective value of the astigmatic power is −0.75 D to −1.25 D. The process data shown in FIG. 14A is selectively applied when the objective value of the astigmatic power is −1.50 D to −2.25 D. The process data shown in FIG. 14B is selectively applied when the objective value of the astigmatic power is −2.50 D to −7.00 D. The process data shown in FIG. 15 is selectively applied when the objective value of the astigmatic power is −7.25 D to −8.00 D. The selection of the process data is performed by the determination means 103.

In each of the axial angle determining processes ((i), (ii), (iii), and (iv)) shown in each of FIGS. 13A, 13B, 14A, 14B, and 15, the upper side shows the angle shift amount from the objective value of the astigmatic axial angle and the lower side shows a stage (examination step) of the astigmatic axial angle measurement performed during the cross cylinder test. In the upper side, a numerical value "0" of the angle shift amount indicates the objective value of the astigmatic axial angle and each of the other numerical values thereof indicates the amount of shift from the objective value. In the lower side, each of numerical values (circle 1, circle 2, . . . ) indicates the stage of the astigmatic axial angle measurement performed during the cross cylinder test. An arrow located beside each of the numerical values in the lower side shows an input content from the lever 6h or the button 6g, which is allowed when the axial angle corresponding to the corresponding numeral value is applied. More specifically, an arrow indicating the right direction (left direction) exhibits the tilt of the lever 6h to the right (left) and an arrow indicating the upper direction exhibits the pressing down of the button 6g.

A numerical value surrounded by a broken line on the upper side exhibits a result obtained by measurement of the astigmatic axial angle of each of the eyes to be examined EL and ER when the input content is set by the person to be examined 4 in each of the stages shown in the lower side. In other words, the plurality of stages shown in the lower side correspond to processes necessary to determine the astigmatic axial angle surrounded by the broken line from the result obtained by measurement on the eyes to be examined EL and ER.

The determination means 103 of the control portion 80 compares the input content from the lever 6h or the like in each of the stages of the astigmatic axial angle measurement with the axial angle determination process data. When the input content coincides with the direction indicated by the arrow shown in the process data, the result of determination by the determination means 103 is "OK" and sends a signal to the optical head section controlling means 104. Upon receiving the signal, the optical head section controlling means 104 controls the VCC lens driving mechanism 84L to change the current astigmatic axial angle of the VCC lens 59 to an astigmatic axial angle used in the next stage. On the other hand, when the input content from the lever 6h or the like is different from the direction indicated by the arrow shown in the process data, the result of determination by the determination means 103 is "error" and transmits a signal to the output control means 105. Upon receiving the signal, the output control means 105 executes error output processing as described later.

A specific example of the above-mentioned processings will be described. In the axial angle determination process (i) shown in FIG. 13A, an astigmatic axial angle shifted from the objective value of the astigmatic axial angle by 40° is applied in a first stage (test stage indicated by circle 1). The amount of shift of 40° is set when the objective value of the astigmatic power is −0.25 D (see FIG. 11). Although the amount of shift of 30° is set when the objective value of the astigmatic power is −0.50 D, the amount of shift of 40° which is equal to that in the case of −0.25 D is applied in this embodiment.

In the first stage, the appearance state of the cross cylinder test chart S is recognized by the person to be examined 4 with a state in which the astigmatic axial angle shifted by the amount of shift of 40° is applied. After that, the positive (or negative) axial angle of the VCC lens 59 is reversed to the negative (or positive) axial angle thereof by the optical head section controlling means 104 and the appearance state is recognized in such a state. If necessary, the two states are alternately caused. Then, voice navigation information for promoting the input of content associated with the state in which the appearance state is clearer is outputted. For example, when the appearance state is clearer in the state in which the amount of shift is 40°, the lever 6h is tilted to the left. When the appearance state is clearer in the reversed state, the lever 6h is tilted to the right. When both the appearance states are equal to each other, voice navigation information for promoting the pressing down of the button 6g is clearer is outputted.

When the input operation is performed by the lever 6h or the button 6g, the determination means 103 compares the input content with the process data for the axial angle determination process (i) shown in FIG. 13A. Here, the arrow in the first stage indicates the right direction. Therefore, when the lever 6h is tilted in the right direction, the result of determination by the determination means 103 is "OK". Then, the astigmatic axial angle of the VCC lens 59 is shifted by the amount of shift (−20°) in a next stage (circle 2: second stage) to shift the examination to the next stage. On the other hand, when the lever 6h is tilted to the left or when the button 6g is pressed down, the result of determination by the determination means 103 is "error". Then, the error output processing is executed.

At this time, for example, the following processing can be applied as the error output processing. (1) A message such as "Please input again" is outputted to promote the reentry by the person to be examined 4. (2) The cross cylinder test is skipped (the objective values of the astigmatic power and the astigmatic axial angle are used as final results obtained by examination). (3) An error determination result is informed from the liquid crystal monitor 64q and/or the voice output portion 86 to an examination assistant to teach an operating method and the like to the person to be examined 4. (4) A conventional training screen is displayed on the liquid crystal monitor 64q (or the liquid crystal monitor 64l or 64r) to train the person to be examined 4.

Note that the liquid crystal monitor 64q and the voice output portion 86 compose an informing means 120 for informing an error determination result made by the determination means 103. The liquid crystal monitor 64q composes a display means for displaying a training screen.

When error determination is made in the first stage, it may be meant that the person to be examined 4 does not understand the content of the cross cylinder test and the operating methods of the lever 6h and the like. That is, as described above, one of the pair of projection images of the cross cylinder test chart S which are indicated in the first stage is clearly visually recognized and the other thereof is visually recognized in the blurred state. In the case of the axial angle determination process (i) shown in FIG. 13A, the first projection image indicated when the amount of shift is 40° should be visually recognized with the blurred state and the projection image indicated when the astigmatic axis is reversed should be clearly visually recognized. Therefore, when information showing that the projection image indicated when the amount of shift is 40° is clearer (lever 6h is tilted to the left) or when both the projection images are equally clear (button 6g is pressed down) is inputted, it is expected that the person to be examined 4 does not understand the cross cylinder test itself or the input operation methods.

In contrast to this, when no error determination is made in the first stage, that is, when the determination result is "OK", it can be expected that the person to be examined 4 understands the content of the cross cylinder test or the input operation methods. Therefore, it can be expected that the examination in the first stage of the cross cylinder test in this embodiment, that is, the examination in a state in which the initial value is applied corresponds to training for understanding examination contents and the operating methods using the training screen, which is performed before a conventional examination.

When the determination result is "OK" in the first stage, the astigmatic axial angle of the VCC lens 59 is changed to a value shifted from the objective value by −20° to shift the examination to the second stage. As is apparent from the axial angle determination process (i) shown in FIG. 13A, the amount of shift in the second stage is set to a value in which the amount of shift two times larger than the permissible error is applied in a reverse direction (reversal of sign (±)). For example, when the objective value of the astigmatic axial angle is 30°, the astigmatic axial angle (initial value) in the first stage is set to 70° (=30°+40°) and the astigmatic axial angle in the second stage is set to 10° (=30°−20°).

In the second stage, an appearance state of the cross cylinder test chart S is recognized by the person to be examined 4 in a state in which the astigmatic axial angle shifted by the amount of shift of −20° is applied. After that, the positive (or negative) axial angle of the VCC lens 59 is reversed to the negative (or positive) axial angle thereof and an appearance state is recognized with such a state. Information showing a clearer appearance state of the appearance states is inputted as an input content by the lever 6h or the like.

When the content inputted by the lever 6h or the like in the second stage is "left", it coincides with the direction indicated by the arrow in the second stage (circle 2) of the axial angle determination process (i) shown in FIG. 13A. Therefore, the determination means 103 determines to be "OK" and the astigmatic axial angle of the VCC lens 59 is changed to an angle shifted by the amount of shift of 20° in the third stage (circle 3) to shift the examination to the next stage.

On the other hand, when the input content in the second stage is "right" or "up (equal)", the determination means 103 determines to be "error". Then, the error output processing is executed. For example, any of the above-mentioned processings can be applied as the error output processing.

The examination is similarly executed in the third stage. When the examination is shifted from the third stage to a fourth stage (last stage), the optical head section controlling means 104 desirably controls the VCC lens driving mechanisms 84L and 84R to change the astigmatic power of each of the VCC lenses 59 to a value smaller than the astigmatic power in each of the previous stages. For example, the astigmatic power in each of the stages before the last stage is set to ±0.50 D and the astigmatic power in the last stage is set to ±0.25 D. When the astigmatic power of the VCC lens 59 in the last stage is set to a small value as described above, the degree of blurring of the projection image of the cross cylinder test chart S is reduced, so the person to be examined 4 can visually recognize a clearer projection image. Therefore, the vagueness of the response in the last stage is reduced as compared with the case where the astigmatic power in the previous stage is used without any change. That is, when the astigmatic axial angle of the cross cylinder lens is deviated to some degree from the true value of the astigmatic axial angle of the eye to be examined, the cross cylinder lens having ±0.50 D is effective to significantly show a difference between the two projection images. However, when the astigmatic axial angle of the cross cylinder lens having ±0.50 D is close to the true value, the difference between the two projection images becomes slight, so the two projection images, in each of which the degree of blurring is large are merely compared with each other. This is not suitable. Thus, when the astigmatic axial angle of the cross cylinder lens is close to the true value, it is more preferable to use the cross cylinder lens having ±0.25 D in which the degree of blurring becomes smaller.

When the result of determination by the determination means 103 is "OK" in the fourth stage, a value "0" surrounded by a broken line on the upper side in the axial angle determination process (i) shown in FIG. 13A is used as a result obtained by measurement. A measurement error of the result satisfies both the permissible errors 15° and 10° which are associated with −0.25 D and −0.50 D which are the objective values of the astigmatic powers set by the error setting means 102 (see FIG. 12).

The other determination processes shown in FIGS. 13B to 15 are executed as in the case of the axial angle determination process (i) shown in FIG. 13A. According to each of the determination processes (ii) to (iv) shown in FIG. 13A, a measurement result satisfying both the permissible errors 15° and 10° which are associated with −0.25 D and −0.50 D which are the objective values of the astigmatic powers shown in FIG. 12 is obtained. According to each of the determination processes shown in FIG. 13B, a measurement result satisfying the permissible error 5° which is associated with −0.75 D to −1.25 D which are the objective values of the astigmatic powers shown in FIG. 12 is obtained. According to each of the determination processes shown in FIG. 14A, a measurement result satisfying the permissible error 3° which is associated with −1.50 D to −2.25 D which are the objective values of the astigmatic powers shown in FIG. 12 is obtained. According to each of the determination processes shown in FIGS. 14B and 15, a measurement result satisfying the permissible error 10 which is associated with −2.50 D to −8.00 D which are the objective values of the astigmatic powers shown in FIG. 12 is obtained. As described later, although the astigmatic axial angle is determined in 1° intervals in each of the determination processes shown in FIGS. 14B and 15, a schematic representation is shown therein.

The following factor is taken into consideration in the determination process (iv) shown in FIG. 13A. The determination process is executed for the case where a value obtained by shifting the objective value of the astigmatic axial angle by 40° is used as a result obtained by measurement. In recent years, the measurement precision of an objective optometry apparatus such as an autorefractometer used for objective optometry measurement is improved and a measurement error becomes, for example, about 10°. Therefore, a result obtained by the objective optometry measurement is relied in the determination process (iv) shown in FIG. 13A. When the determination at the amount of shift is 20° in the third stage is "left", the appearance state in the case of the objective value "0" (fourth stage) is recognized once. Then, when it is determined to be "left" even in the case of the objective value "0", the determination made by the person to be examined 4 is respected. Thus, when the examination is to be performed, it is estimated that the amount of shift from the objective value of the astigmatic axial angle of each of the eyes to be examined EL and ER is a value larger than 20°.

The determination processes shown in FIGS. 13A to 15 are parts of the determination processes included in the optometry apparatus 2 according to this embodiment. Here, assume that the objective value of the astigmatic axial angle is expressed by A. When the objective value of the astigmatic power is −0.25 D to −0.50 D, for example, the optometry apparatus 2 includes at least one determination process for obtaining (A+0°) as a result obtained by measurement, at least one determination process for obtaining (A+10°) as the result, at least one determination process for obtaining (A−10° as the result, at least one determination process for obtaining (A+20°) as the result, at least one determination process for obtaining (A−20°) as the result, at least one determination process for obtaining (A+30°) as the result, at least one determination process for obtaining (A−30°) as the result, at least one determination process for obtaining (A+40°) as the result, at least one determination process for obtaining (A−40°) as the result, at least one determination process for obtaining (A+50°) as the result, and at least one determination process for obtaining (A−50°) as the result. When the objective value of the astigmatic power is −0.75 D to −1.25 D, for example, the optometry apparatus 2 includes at least one determination process for obtaining (A+0°) as the result, at least one determination process for obtaining (A+5°) as the result, at least one determination process for obtaining (A−5°) as the result, at least one determination process for obtaining (A+10°) as the result, at least one determination process for obtaining (A−10°) as the result, at least one determination process for obtaining (A+15°) as the result, at least one determination process for obtaining (A−15°) as the result, at least one determination process for obtaining (A+20°) as the result, at least one determination process for obtaining (A−20°) as the result, at least one determination process for obtaining (A+25°) as the result, and at least one determination process for obtaining (A−25°) as the result. When the objective value of the astigmatic power is −1.50 D to −2.25 D, for example, the optometry apparatus 2 includes at least one determination process for obtaining (A+0°) as a result obtained by measurement, at least one determination process for obtaining (A+3°) as the result, at least one determination process for obtaining (A−3°) as the result, at least one determination process for obtaining (A+60) as the result, at least one determination process for obtaining (A−6°) as the result, at least one determination process for obtaining (A+9°) as the result, at least one determination process for obtaining (A−9°) as the result, at least one determination process for obtaining (A+12°) as the result, at least one determination process for obtaining (A−12°) as the result, at least one determination process for obtaining (A+15°) as the result, and at least one determination process for obtaining (A−15°) as the result. When the objective value of astigmatic power is −2.50 D to −7.00 D, for example, the optometry apparatus 2 includes at least one determination process for obtaining (A+0°) as the result, at least one determination process for obtaining (A+1°) as the result, at least one determination process for obtaining (A−1°) as the result, at least one determination process for obtaining (A+2°) as the result, at least one determination process for obtaining (A−2°) as the result, at least one determination process for obtaining (A+3°) as the result, at least one determination process for obtaining (A−3°) as the result, at least one determination process for obtaining (A+4°) as the result, at least one determination process for obtaining (A−4°) as the result, at least one determination process for obtaining (A+5°) as the result, at least one determination process for obtaining (A−5°) as the result, at least one determination process for obtaining (A+6°) as the result, at least one determination process for obtaining (A−6°) as the result, at least one determination process for obtaining (A+7°) as the result, at least one determination process for obtaining (A−7°) as the result, at least one determination process for obtaining (A+8°) as the result, at least one determination process for obtaining (A−8°) as the result, at least one determination process for obtaining (A+9°) as the result, and at least one determination process for obtaining (A−9°) as the result. When the objective value of astigmatic power is −7.25 D to −8.00 D, for example, the optometry apparatus 2 includes at least one determination process for obtaining (A+0°) as the result, at least one determination process for obtaining (A+1°) as the result, at least one determination process for obtaining (A−1°) as the result, at least one determination process for obtaining (A+2°) as the result, at least one determination process for obtaining (A−2°) as the result, at least one determination process for obtaining (A+3°) as the result, at least one determination process for obtaining (A−3°) as the result, at least one determination process for obtaining (A+4°) as the result, at least one determination process for obtaining (A−4°) as the result, at least one determination process for obtaining (A+5°) as the result, at least one determination process for obtaining (A−5°) as the result, at least one determination process for obtaining (A+6°) as the result, at least one determination process for obtaining (A−6°) as the result, at least one determination process for obtaining (A+7°) as the result, at least one determination process for obtaining (A−7°) as the result, at least one determination process for obtaining (A+8°) as the result, at least one determination process for obtaining (A−8°) as the result, at least one determination process for obtaining (A+90) as the result, and at least one determination process for obtaining (A−9°) as the result.

[Operation/Effect]

The operation/effect of the optometry apparatus 2 according to this embodiment will be described.

According to the optometry apparatus 2, in order to perform the cross cylinder test, the initial value of the astigmatic axial angle of the VCC lens 59 is set such that one of the pair of projection images of the cross cylinder test chart S is clearly visually recognized and the other thereof is visually recognized with the blurred state in the first stage of the actual cross cylinder test. Therefore, it is possible to understand the content of the cross cylinder test and train on the operating methods in the first stage, so it is unnecessary to perform the training for the cross cylinder test before the examination and the time therefor is not needed. Thus, the entire examination time can be shortened.

As described above, the training and the examination are performed in an integrated manner, so there is no case where the operating methods and the examination contents which are temporarily understood in the training are forgotten. Therefore, the cross cylinder test can be smoothly performed, thereby shortening the examination time.

When a structure in which the training screen is displayed corresponding to the error determination is used, the understanding of the content of the test and the operating methods can be facilitated through the training for a person to be examined who does not understand them. On the other hand, the cross cylinder test can be smoothly performed on a person to be examined, who understands the content of the test and the operating methods without using the training screen. Therefore, it is possible to shorten the examination time.

According to the optometry apparatus 2, the axial angle determination process is selected based on the permissible error associated with the astigmatic power of the eye to be examined, so there is no case where the astigmatic axial angle is measured with excessive measurement precision. Therefore, the cross cylinder test can be speedily performed as compared with a conventional case, so that the examination time can be shortened.

When the astigmatic axial angle measurement is in the last stage, the astigmatic power of the VCC lens 59 is changed to a value smaller than that in the previous stage. Therefore, it is possible to reduce the vagueness of the response of the person to be examined in the last stage, with the result that the examination time can be shortened. As described above, when smaller astigmatic power is applied in the last stage, the blurred states of the pair of projection images to be compared become smaller, so the examination is completed while the projection images are more clearly recognized. Thus, the person to be examined can complete the examination in a clearer sense as compared with a conventional case, so that the reliability of a spectacle lens produced on the basis of the examination can be prevented from being degraded.

When the response of the person to be examined is deviated from the objective value of the astigmatic axial angle (for example, in the case of the determination process (iv) shown in FIG. 13A), the appearance state in the case of the objective value is recognized once. Therefore, when the response is wrong, it can be corrected. On the other hand, when it is determined that the response is reasonable, the response of the person to be examined 4 is respected and then the examination can be continued.

[Modified Examples]

In the above-mentioned embodiment, the optometry apparatus having the function for simultaneously performing the objective optometry measurement on both eyes and the function for performing the subjective optometry measurement only by the person to be examined using the screen navigation system or the voice navigation system is described. The optometry apparatus according to the present invention is not limited to this. For example, the structure according to the present invention can be used for an optometry apparatus of a type in which optical elements are selectively disposed in front of the eye to be examined (for example, an optometry unit of a subjective optometry apparatus described in JP 2002-253503 A).

In the above-mentioned embodiment, the variable cross cylinder lens (VCC lens) is used to form the pair of projection images of the cross cylinder test chart S. A cross cylinder lens of a type in which the front and rear surfaces of the lens is reversed to each other may be used. In such a case, for example, it is necessary to provide an additional optical member (such as a cylindrical lens) for changing the astigmatic power, so the optical system is complicated. Therefore, it may be desirable to use the variable cross cylinder lens.

An arbitrary input device such as a control panel and a trackball can be used for the operating means instead of to the joystick lever 6h and the button 6g.

Each of the liquid crystal monitors 64l and 64r provided in front of the optical head sections 5l and 5r, respectively, a monitor of the computer apparatus (not shown), the liquid crystal display device 53 of each of the optical head sections 5l and 5r, or the like can be used as the display means for informing the error determination result and displaying the training screen instead of the liquid crystal monitor 64q erected on the optometry table 1.

In the above-mentioned embodiment, the initial value setting data, the permissible error setting data, and the axial angle determination process data are set in the objective value of the astigmatic power having a range of –0.25 D to –8.00 D. The data may be set in another objective value range. Although the data is set in steps of 0.25 D, the present invention is not limited to this. With respect to the initial value setting data, the same angle shift amount is set for a plurality of objective values as in the case where the objective value of the astigmatic power is –0.25 D and the case where it is –0.50 D. Different angle shift amounts may be set for the respective objective values. This is the same with respect to the permissible error setting data and the axial angle determination process data.

In the above-mentioned embodiment, in the last stage of the astigmatic axial angle measurement, the astigmatic power is changed to a value smaller than that in the previous stage. The changing of the astigmatic power is not limited to that in the last stage. That is, the astigmatic power of the cross cylinder lens after a predetermined stage of the astigmatic axial angle measurement can be changed to a value smaller than the astigmatic power in the stage before the predetermined stage. The "predetermined stage" is preferably a stage in which the astigmatic axial angle measurement progresses and the astigmatic axial angle of the cross cylinder lens is close to the true value of the astigmatic axial angle of the eye to be examined.

The above-mentioned detailed structures are merely structural examples for implementing the optometry apparatus according to the present invention. Thus, various modifications can be made without departing from the gist of the present invention.

What is claimed is:

1. An optometry apparatus, comprising:
   an optical system for projecting an index for cross cylinder test to an eye to be examined;
   a cross cylinder lens for forming one pair of projection images of the index by a change in astigmatic axial angle while predetermined astigmatic power is set, the cross cylinder lens being disposed on an optical axis of the optical system;
   operating means for inputting a result of comparison between appearance states of the pair of projection images of the index, wherein the optometry apparatus is adapted to perform a subjective measurement of measuring an astigmatic axial angle of the eye to be examined based on an input content from the operating means;
   initial value setting means for determining an astigmatic axial angle of the cross cylinder lens which causes one of the pair of projection images of the index to be clearly visually recognized and causes the other of the pair of projection images of the index to be visually recognized in a blurred state based on an objective value of astigmatic power of the eye to be examined and an objective value of the astigmatic axial angle of the eye to be examined, which are measured in advance, and for setting the determined astigmatic axial angle as an initial value for the subjective measurement of an astigmatic axial angle measurement;
   storing means for storing an amount of shift from the objective value of the astigmatic axial angle, which is necessary to cause the one of the pair of projection images to be clearly visually recognized and cause the other of the pair of projection images to be visually recognized in the blurred state, in association with the objective value of the astigmatic power in advance,
   wherein the initial value setting means determines the amount of shift from the storing means, said amount being associated with the previously measured objective value of the astigmatic power of the eye to be examined, and shifts the previously measured objective value of the astigmatic axial angle of the eye to be examined by the determined amount of shift to determine the initial value; and
   control means for changing the astigmatic axis angle of the cross cylinder lens beginning from the initial value.

2. An optometry apparatus according to claim 1, further comprising determination means for determining whether the input content from the operating means is different from a preset input content from comparison between appearance states of the pair of projection images while the initial value is set.

3. An optometry apparatus according to claim 2, wherein said control means controls the cross cylinder lens to change the astigmatic axial angle when the input content via the operating means is identical with the preset input content.

4. An optometry apparatus according to claim 3, further comprising error setting means for setting a permissible error for the astigmatic axial angle measurement of the eye to be examined based on the objective value of the astigmatic power,
   wherein the control means controls the cross cylinder lens to change stages of the astigmatic axial angle so that a measurement error of the astigmatic axial angle of the eye to be examined is kept within the permissible error.

5. An optometry apparatus according to claim 4, wherein the permissible error is set so that residual astigmatism, which is caused when the objective value of the astigmatic power and the objective value of the astigmatic axial angle are corrected by a corrective lens and an astigmatic axial angle of the corrective lens is shifted, is within a first predetermined range, and that the amount of change in spherical power caused when the objective value of the astigmatic power and the objective value of the astigmatic axial angle are combined with astigmatic power of the corrective lens and an astigmatic axial angle of the corrective lens is within a second predetermined range.

6. An optometry apparatus according to claim 5, wherein the first predetermined range for the residual astigmatism is within −0.25 diopters and the second predetermined range for the amount of change in spherical power is smaller than ±0.25 diopters.

7. An optometry apparatus according to claim 3, wherein the control means changes the astigmatic axis angle of the cross cylinder over several stages, and the control means changes the astigmatic power of the cross cylinder lens in a stage after a predetermined stage of the astigmatic axial angle measurement to a value smaller than the astigmatic power in a stage before the predetermined stage.

8. An optometry apparatus according to claim 4, wherein the control means changes the astigmatic axis angle of the cross cylinder over several stages, and the control means changes the astigmatic power of the cross cylinder lens in a stage after a predetermined stage of the astigmatic axial angle measurement to a value smaller than the astigmatic power in a stage before the predetermined stage.

9. An optometry apparatus according to claim 5, wherein the control means changes the astigmatic axis angle of the cross cylinder over several stages, and the control means changes the astigmatic power of the cross cylinder lens in a stage after a predetermined stage of the astigmatic axial angle measurement to a value smaller than the astigmatic power in a stage before the predetermined stage.

10. An optometry apparatus according to claim 6, wherein the control means changes the astigmatic axis angle of the cross cylinder over several stages, and the control means changes the astigmatic power of the cross cylinder lens in a stage after a predetermined stage of the astigmatic axial angle measurement to a value smaller than the astigmatic power in a stage before the predetermined stage.

11. An optometry apparatus according to claim 1, wherein said control means controls the cross cylinder lens to change the astigmatic axial angle when the input content via the operating means is identical with the preset input content.

12. An optometry apparatus according to claim 11, further comprising error setting means for setting a permissible error for the astigmatic axial angle measurement of the eye to be examined based on the objective value of the astigmatic power,
wherein the control means controls the cross cylinder lens to change stages of the astigmatic axial angle so that a measurement error of the astigmatic axial angle of the eye to be examined is kept within the permissible error.

13. An optometry apparatus according to claim 12, wherein the permissible error is set so that residual astigmatism, which is caused when the objective value of the astigmatic power and the objective value of the astigmatic axial angle are corrected by a corrective lens and an astigmatic axial angle of the corrective lens is shifted, is within a first predetermined range, and that the amount of change in spherical power caused when the objective value of the astigmatic power and the objective value of the astigmatic axial angle are combined with astigmatic power of the corrective lens and an astigmatic axial angle of the corrective lens is within a second predetermined range.

14. An optometry apparatus according to claim 13, wherein the first predetermined range for the residual astigmatism is within −0.25 diopters and the second predetermined range for the amount of change in spherical power is smaller than ±0.25 diopters.

15. An optometry apparatus according to claim 11, wherein the control means changes the astigmatic axis angle of the cross cylinder over several stages, and the control means changes the astigmatic power of the cross cylinder lens in a stage after a predetermined stage of the astigmatic axial angle measurement to a value smaller than the astigmatic power in a stage before the predetermined stage.

16. An optometry apparatus according to claim 12, wherein the control means changes the astigmatic axis angle of the cross cylinder over several stages, and the control means changes the astigmatic power of the cross cylinder lens in a stage after a predetermined stage of the astigmatic axial angle measurement to a value smaller than the astigmatic power in a stage before the predetermined stage.

17. An optometry apparatus according to claim 13, wherein the control means changes the astigmatic axis angle of the cross cylinder over several stages, and the control means changes the astigmatic power of the cross cylinder lens in a stage after a predetermined stage of the astigmatic axial angle measurement to a value smaller than the astigmatic power in a stage before the predetermined stage.

18. An optometry apparatus according to claim 14, wherein the control means changes the astigmatic axis angle of the cross cylinder over several stages, and the control means changes the astigmatic power of the cross cylinder lens in a stage after a predetermined stage of the astigmatic axial angle measurement to a value smaller than the astigmatic power in a stage before the predetermined stage.

19. An optometry apparatus according to any one of claims 1 and 2-7 wherein the storing means stores the amount of shift and the associated objective value of the astigmatic power in such a manner that, the larger an absolute value of the objective value of
the astigmatic power, the smaller the amount of shift from the objective value of the astigmatic axial angle.

20. An optometry apparatus according to claim 1, wherein if the predetermined input content is input via the operating means, the control means obtains a next amount of shift from the current amount of shift by decreasing or retaining an absolute value of the current amount of shift, adds the next amount of shift to the objective value of the astigmatic axial angle to obtain a value, and sets the astigmatic axial angle of the cross cylinder lens to the obtained value, and
wherein the optometry apparatus measures the astigmatic axial angle of the eye to be examined as the astigmatic axial angle of the cross cylinder lens with which the clarifies of the pair of the projection images are substantially equal, through changing the astigmatic axial angle of the cross cylinder lens by the control means.

21. An optometry apparatus according to claim 20, wherein if the predetermined direction is input via the operating means, the control means decreases or retains an absolute value of the current amount of shift, reverses positive and negative of the current amount of shift, and adds the next amount of shift to the objective value of the astigmatic axial angle.

22. An optometry apparatus according to claim 20, wherein if the predetermined input content is input via the operating means, the control means, for the astigmatic axial angle set as the initial value, decreases an absolute value of the current amount of shift, reverses positive and negative of the current amount of shill and adds the next amount of shift to the objective value of the astigmatic axial angle.

23. An optometry apparatus according to claim 20, wherein if the predetermined input content is input via the operating means and the previous amount of shift and the current amount of shift are opposite in terms of positive and negative, the control means decreases an absolute value of the current amount of shill and adds the next amount of shift to the objective value of the astigmatic axial angle.

* * * * *